(12) United States Patent
Gum et al.

(10) Patent No.: US 9,508,145 B2
(45) Date of Patent: Nov. 29, 2016

(54) DETERMINATION OF A CHANGE OF POSITION OF A BONY STRUCTURE IN RADIATION THERAPY

(75) Inventors: Franz Gum, Munich (DE); Stephan Erbel, Munich (DE)

(73) Assignee: Brainlab AG, Feldkirchen (DE)

( * ) Notice: Subject to any disclaimer, the term of this patent is extended or adjusted under 35 U.S.C. 154(b) by 132 days.

(21) Appl. No.: 14/001,695

(22) PCT Filed: Jun. 15, 2011

(86) PCT No.: PCT/EP2011/059950
§ 371 (c)(1),
(2), (4) Date: Oct. 28, 2013

(87) PCT Pub. No.: WO2012/095190
PCT Pub. Date: Jul. 19, 2012

(65) Prior Publication Data
US 2014/0037173 A1 Feb. 6, 2014

(30) Foreign Application Priority Data

Jan. 12, 2011 (EP) .................... PCT/EP2011/050351

(51) Int. Cl.
*G06K 9/00* (2006.01)
*G06T 7/00* (2006.01)
(Continued)

(52) U.S. Cl.
CPC ............. *G06T 7/0016* (2013.01); *A61B 6/547* (2013.01); *A61N 5/1049* (2013.01);
(Continued)

(58) Field of Classification Search
None
See application file for complete search history.

(56) References Cited

U.S. PATENT DOCUMENTS

2007/0291895 A1* 12/2007 Yin ........................ A61B 6/025
378/20
2009/0285366 A1 11/2009 Essenreiter et al.
(Continued)

FOREIGN PATENT DOCUMENTS

EP 1 832 313 9/2007
JP EP 1832313 A1 * 9/2007 .......... A61N 5/1049
(Continued)

OTHER PUBLICATIONS

International Search Report for International Application No. PCT/EP2011/059950 dated Sep. 27, 2011.
(Continued)

*Primary Examiner* — Stephen R Koziol
*Assistant Examiner* — Amandeep Saini
(74) *Attorney, Agent, or Firm* — Tucker Ellis LLP

(57) ABSTRACT

The present invention refers to a data processing method for use in the field of radiation therapy and for determining a relative position between the position of the bony structure and a reference position at a monitoring time, the relative position being referred to as monitoring bone position, wherein an anatomical structure of a patient includes the bony structure and a treatment body part to be treated by at least one treatment beam of a treatment device, the reference position having a defined relative position with respect to an actual arrangement of at least one position of the at least one treatment beam; the data processing method being constituted to be performed by a computer and comprising the following steps: •providing CBCT image data describing a three-dimensional CBCT image of the bony structure, the CBCT image representing the bony structure at a pre-alignment time; •providing x-ray image data describing at least one two-dimensional x-ray image of the anatomical structure, the at least one two-dimensional x-ray image representing the bony structure (110) and the x-ray image data being generated at the monitoring time; •providing imaging position data comprising at least one of CBCT position data and x-ray geometry data, CBCT position data describing the relative position between the CBCT image and the actual arrangement and the x-ray geometry data describing a positional relationship between the actual arrangement and at least one imaging geometry, referred to as x-ray imaging geometry, given for generating the at least one x-ray image; •determining the relative position between the bony structure and the reference position at the monitoring time on the basis of the CBCT image data, the x-ray image data and the imaging position data.

12 Claims, 3 Drawing Sheets

(51) Int. Cl.
*A61N 5/10* (2006.01)
*A61B 6/00* (2006.01)

(52) U.S. Cl.
CPC .......... *A61N 5/1064* (2013.01); *A61N 5/1069* (2013.01); *A61N 2005/1061* (2013.01); *A61N 2005/1062* (2013.01)

(56) References Cited

U.S. PATENT DOCUMENTS

| | | | |
|---|---|---|---|
| 2013/0287167 | A1 | 10/2013 | Gum et al. |
| 2014/0037173 | A1 | 6/2014 | Gum et al. |

FOREIGN PATENT DOCUMENTS

| | | |
|---|---|---|
| WO | 2006/039009 | 4/2006 |
| WO | 2008/063299 | 5/2008 |
| WO | 2010/143400 A1 | 12/2010 |

OTHER PUBLICATIONS

Yeung A R et al., "Tumor Localization Using Cone-Beam CT Reduces Setup Margins in Conventionally Fractionated Radiotherapy for Lung Tumors", International Journal of Radiation: Oncology Biology Physics, vol. 74, No. 4, Jul. 15 2009, pp. 1100-11007, Pergamon Press, USA.

Wang Z et al., "Refinement of Treatment Setup and Target Localization Accuracy Using Three-Dimensional Cone-Beam Computed Tomography for Stereotactic Body Radiotherapy", International Journal of Radiation; Oncology Biology Physics,vol. 73, No. 2, Feb. 1, 2009, pp. 571,577, Pergamon Press, USA.

European Patent Office, Substantive examination,EP application No. 11700409, mail date: Oct. 28, 2015, pp. 1-10.

United States Patent and Trademark Office, Notice of Allowance and Fee(s) Due, U.S. Appl. No. 13/977,252, filed Jun. 28, 2013, first named inventor: Franz Gum, Mail Date: Mar. 2, 2016.

* cited by examiner

DETERMINATION OF A CHANGE OF POSITION OF A BONY STRUCTURE IN RADIATION THERAPY

This application is a national phase of International Application No. PCT/EP2011/059950 filed Jun. 15, 2011 and published in the English language.

The present application relates to the field of radiation therapy. In more detail, the application relates to the determination of a relative position between a position of a bony structure at a monitoring time and a reference position. This relative position is referred to as "monitoring bone position". The change of the relative position is referred to as "bone change".

The object of the present invention is to determine the monitoring bone position. Preferably, also the bone change is determined.

This object is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

Preferably, the reference position has a defined relative position with respect to the position of an actual arrangement of at least one treatment beam position and can be identical or different to the position of the actual arrangement. "Defined relative position" means in particular that the relative position is fixed (non-changing), in particular at least within a time interval for which the bone change is determined (preferably at least between the pre-alignment time and the monitoring time or at least between the alignment time and the monitoring time or at least between the previous monitoring time and the monitoring time). "Fixed" means in particular that the relative position between the reference position and the position of the actual arrangement does not change, in particular at least within one of the aforementioned time intervals. The term "defined relative position" encompasses in particular a predefined relative position which is provided to the data processing method (and in particular predefined before the pre-alignment time) and in particular the determination of which is not part of the data processing method like the target position or encompasses that the relative position between the actual arrangement and the reference position can be determined in particular by one or more steps of the data processing method, like the bone CBCT position or alignment bone position (see below). Preferably, reference position data are provided which describe the relative position between the reference position and the position of the actual arrangement (in particular if the reference position differs from the position of the actual arrangement. The monitoring bone position is preferably determined (also) based on the reference position data, in particular if the reference position differs from the position of the actual arrangement. The reference position data describe in particular that the bone CBCT position or the alignment bone position or the position of the actual arrangement or the target position or the previous monitoring bone position (in particular the preceding monitoring bone position) is the reference position.

Advantageously, the present invention allows to determine position and/or the change of position of the bony structure in order to improve the radiation therapy by means of at least one treatment beam. The at least one treatment beam adopts positions (referred to as beam positions) as defined by an arrangement of at least one beam position. The positions, in particular the relative positions described herein, for instance the monitoring bone position, the position of the bony structures, the reference position and/or the position of the arrangement can be described in a reference system. The reference system can be a reference system in which the actual arrangement is at rest. The reference system can be in particular a reference system in which an intersection point of the treatment beams is at rest (in case the actual arrangement comprises more than one treatment beam). The reference system can be for instance also a reference system in which the bony structure or the treatment body part is at rest or can be a reference system in which for instance the room (in which the treatment by the at least one treatment beam takes place) is at rest. In particular, the position of the bony structure and the reference position can be described relative to the actual arrangement. However, this is not obligatory. The position of the bony structure and the reference position can also be described for instance relative to the room or the treatment device or the body.

According to an advantageous aspect of the present invention, the determined bone change is considered as an indicator that the treatment body part has changed its position. In particular in case the determined bone change is not equal zero, there is a risk that the treatment body part is not in the desired (in particular planned) relative position with respect to the arrangement. Alternatively or additionally, it can be for instance checked whether the determined monitoring bone position corresponds to a target position. Thus, according to an advantageous embodiment, the step of determination of the bone change and/or the monitoring bone position can be followed by further steps like for instance issuing a warning signal, correcting the position of the patient and/or the arrangement, stopping the radiation therapy etc. These aspects will be discussed in more detail later.

The bone change can be described by a vector which describes the direction and preferably the amount of change of position of the bone structure or just by a scalar which describes the amount. The bone change is in particular the change of the relative position within a predefined time interval which ends in particular at the monitoring time. The bone change is in particular defined to be the change of the relative position which occurred from a previous time (in particular pre-alignment time and more preferably alignment time or previous monitoring time (see below)) to the monitoring time. The step of determining the bone change can comprise the step of determining whether there is a change. To this end, the amount of the change can be checked to be above or below a predefined threshold (which can be zero or more) and/or the direction of the change can be determined to be within a certain range or to be the same as before. In order to determine the bone change, in particular the relative position (referred to as first relative position or monitoring bone position) between the bony structure at the monitoring time and the reference position is compared with the relative position (referred to as second relative position or previous relative position) between the position of the bony structure at a previous time and the reference position. The step of comparison comprises in particular to determine a difference between the first and second relative position (for instance by determining the difference of a first vector representing the first relative position in a reference system and a second vector representing the second relative position in the reference system). The second relative position can be for instance one of the following example positions), if the reference position is the position of the actual arrangement: the bone CBCT position, the alignment bone position, the relative position between the bony structure at the previous monitoring time and the position of the actual arrangement or the target position (see below. If the reference position differs from the position of the actual arrangement, the second relative position can be determined based on one of the example positions and based on the (defined) relative position between the reference position and the position of the actual arrangement (e.g. by determining the difference between a vector describing the position of a selected one of the example positions and a vector describing the reference position, e.g. in a reference system in which the position of the actual arrangement is at rest).

In the following, just as a non-limiting and preferred example, the monitoring bone position is assumed to be the relative position between the position of the bony structure at the monitoring time and position of the actual arrangement. Of course, the reference position used for determining the monitoring bone position can differ from the position of the actual arrangement and can in particular adopt any of those examples given herein for the reference position. If the reference position used for determining the monitoring bone position differs from the position of the actual arrangement, then the monitoring bone position can be determined based on the relative position between the position of the bony structure and the position of the actual arrangement at the monitoring time and based on the defined relative position between the reference position and the position of the actual arrangement. To this end for instance a difference between a vector describing the position of the reference position and a vector describing the aforementioned relative position between the position of the bony structure and the position of the actual arrangement at the monitoring time can be determined for instance in a reference system in which the position of the actual arrangement is at rest.

The present invention also relates to the field of control of the treatment beam. The treatment beam treats body parts to be treated which are referred to in the following as "treatment body parts". These body parts are in particular body parts of a patient, i.e. anatomical body parts.

The present invention relates to the field of medicine and in particular to the use of beams, in particular radiation beams in order to treat parts of the body. Ionizing radiation is in particular used for this purpose. In particular, the treatment beam comprises or consists of ionizing radiation. The ionizing radiation comprises or consists of particles (for example sub atomic particles or ions) or electromagnetic waves which are energetic enough to detach electrons from atoms or molecules and so ionize them. The treatment beam, in particular the treatment radiation is in particular used in radiation therapy (also called radiotherapy), in particular in the field of oncology. For the treatment of cancer in particular, parts of the body comprising the tumor are treated by using ionizing radiation. The tumor is an example for a treatment body part. The treatment beam is preferably controlled to pass through the treatment body part.

The arrangement of at least one beam position comprises (in particular consists of) at least one beam position, in particular a discrete set of beam positions or a continuous multiplicity (manifold) of beam positions. The at least one beam position is the at least one position of the at least one treatment beam. That is, during treatment, the at least one treatment beam adopts the at least one beam position defined by the arrangement. In case of more than one beam position, the adoption is performed in particular sequentially in particular in case there is just one beam source to emit a treatment beam. If there are several beam sources, beam positions can also be adopted simultaneously by the several treatment beams during the treatment. The arrangement of the at least one beam position which defines the at least one beam position relative to the treatment device, in particular during (actual) treatment (in particular during a treatment session, which is also referred to as a fraction) is referred to as actual arrangement. In particular, the actual arrangement has a point of intersection in which all treatment beams (in case of more than one) of the actual arrangement intersect. In particular, the determined position is described relative to the position of the intersection point, for instance in a reference system which has the intersection point in its origin. The intersection point corresponds in particular to an isocenter of the treatment device. An "isocentric rotation" is understood to be a rotation of the patient around a vertical axis which passes through the isocenter (intersection point of the treatment beams). Advantageously, in case of an isocentric rotation, the method in accordance with the invention allows to determine if there is a change of the monitoring bone position which does not only result from the isocentric rotation. In that case, the reference position is preferable the alignment bone position (see below), i.e. the position of the bony structure after the isocentric rotation which has been performed for alignment.

The defined planned relative bone position is a relative position between the bony structure and a planned arrangement of beam positions. In particular the above-mentioned treatment planning (e.g. performed by a treatment planning system before the treatment, for instance based on computed tomographic images (referred to as CT images)) results in the planned relative bone position between the bony structure and the planned arrangement. Of course, the user (e.g. medical specialist) can set a new planned relative bone position e.g. after studying the CBCT image. In the following, the term "planned relative bone position" covers both alternatives, a planned relative bone position (referred to as "a original planned relative bone position") purely based on planning image data (e.g. CT image) or an updated planned relative position set by a user or determined as described later. According to an embodiment, the reference position is a target position. The target position is a relative position between the bony structure and the actual arrangement. The target position is in particular the original planned relative bone position or the updated planned relative bone position. In particular the actual arrangement is set to comprise the same number of beam positions as the planned arrangement. In particular in case the planned arrangement comprises two or more beam positions, the relative positions between the beam positions is set to be identical in the planned arrangement and in the actual arrangement.

The position of a part or a structure of the anatomical structure can in particular be represented (in particular described) by the position of the center (e.g. center of mass) of the part or of the structure.

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion. The data are in particular data which represent physical properties and/or are generated from technical signals. The technical signals are in particular generated by means of technical detection devices and/or analytical devices.

Where data are "provided", this means that they are ready for use by the method or program in accordance with the invention. The data can achieve this state of being "ready for use" by for example being generated (e.g. by a CT or CBCT or MRT), in particular detected or captured (for example by analysis apparatuses) or by being input (for example via interfaces). The data can also achieve the state of being provided by being stored in a data storage (for example a ROM, RAM, CD and/or hard drive) and thus ready for use within the framework of the method or program in accordance with the invention. The expression "providing data" encompasses (within the framework of a data processing method) in particular that the data are determined by the data processing method or program. The meaning of "providing data" in particular encompasses also that the data are received by the data processing method or program, in particular to further process the data by the data processing method or program. Thus "providing data" can mean for instance to wait for a reception of data and to receive the data. The received data can be for instance inputted by the interface. "Providing data" can also mean that the data processing method or program performs steps to (actively) acquire the data from a data source, for instance a data storage (for instance ROM, RAM, data base, hard disk etc.) or via the interface (for instance from another computer or a network).

As mentioned above, the determined bone change can be used as an indicator for a change of position of the treatment body part relative to the actual arrangement. In particular, under the assumption that there is a fixed relative position between the bony structure and the treatment body part, the data processing method can be used to determine the position of the treatment body part relative to the actual arrangement. This position of the treatment body part is referred to as "actual relative position".

The position of the bony structure (during treatment) is referred to as actual relative bony position. The actual relative bony position can change from time to time. The actual relative bony position is the relative position between the bony structure and the reference position. The actual relative bony position which is given at a time referred to as monitoring time is referred to as herein monitoring bone position.

The position of the treatment body part (during treatment) referred to as actual relative tissue position can change from time to time. The actual relative tissue position is the relative position between the treatment body part and the actual arrangement. The actual relative tissue position which is given at a time referred to as monitoring time is referred to as herein monitoring tissue position. In particular the treatment body part is a soft tissue part (e.g. a tumor) of the anatomical structure of the patient. The term "soft tissue" means herein in particular that the soft tissue part is not part of a bony structure of the anatomical body of the patient.

The bony structure can change its geometry (size and/or shape) between the planning time and the pre-alignment time and also during the treatment. Generally, the change of the geometry of the bony structure from the planning time to the pre-alignment time will be larger than the change of the bony structure from the pre-alignment time to the monitoring time. According to an advantage of the present invention, the geometry of the bony structure at the pre-alignment time is used for determining the position of the bony structure based on the x-ray image data. In particular, the geometry of the bony structure described by the CBCT image data is compared with the geometry of the bony structure described by the x-ray image data in order to determine the position of the bony structure relative to the referenced position. Advantageously, a higher accuracy of determining the position of the bony structure can be achieved in this manner. The step of comparing the geometry of the bony structure described by the CBCT image data and the geometry of the bony structure described by the x-ray image data can include the step of generating DRRs and/or a step of image morphing as described below.

As mentioned above, CBCT image data (also just referred to as CBCT data) are preferably provided. The CBCT image data describe a three-dimensional CBCT image of a region which includes the bony structure, in particular the anatomical structure. Thus, the CBCT image describes the bony structure, in particular the anatomical structure. The CBCT image represents the bony structure, in particular the anatomical structure at a time (referred to as pre-alignment time) when the CBCT image was generated. Preferably, the CBCT image data include information (e.g. segmentation data, see below) on the position of the bony structure within the CBCT image. In particular, the CBCT image data describe the position of the bony structure within the CBCT image and/or in particular allow the determination of this position. That is, for instance, if the relative position between the CBCT image and another position, e.g. the reference position (e.g. the position of the actual arrangement) is known, then the position of the bony structure relative to the reference position can be determined based on the CBCT image data. The three-dimensional CBCT image represents the bony structure and in particular the anatomical structure which includes the treatment body part and the bony structure. The term "bony structure" can encompass a complete set of all anatomical bony elements included in the anatomical structure and/or represented by the CBCT image or can just mean one or more parts of the "complete set". The one or more parts can be in particular landmarks, the position, in particular orientation of which is definable. Landmark is a defined element of an anatomical body part which is always identical or recur with a high degree of similarity in the same anatomical body part of multiple patients. Typical landmarks are for example the tips of the transverse processes and/or dorsal process of a vertebrae. The treatment body part and the bony structure are represented by the CBCT image in a relative position to each other.

The abbreviation CBCT stands for cone-beam computed tomography and is in particular used in the field of image guided radiation therapy. Advantageously, the present invention is directed to this field of image guided radiation therapy (IGRT). A CBCT device (used for generating the CBCT images) is in particular arranged in a known position relative to the actual arrangement of at least one beam position. The actual arrangement of at least one beam position is in particular set in accordance with a treatment plan to adopt a particular position with respect to a treatment device which issues the treatment beam in accordance with the arrangement. Preferably, the relative position between the CBCT device and the treatment device is known which results in that the relative position between the actual arrangement and the CBCT device (and thus the CBCT image) is known.

The CBCT (CBCT image data and optionally the CBCT position data) allows in particular to determine the position of the bony structure with respect to the actual arrangement. This position is referred to as bone CBCT position. According to an embodiment, the bone CBCT position is the reference position. In particular, deviations of the actual relative position of the bone CBCT position from the planned relative position (at the pre-alignment time) can be determined. In particular, the CBCT acquires a plurality of projections over the anatomical structure (volume of interest). In particular, the two-dimensional projections are reconstructed into a three-dimensional CBCT image (three-dimensional volume) in particular corresponding to data referred to as pre-data (e.g. CT image data) by using reconstruction strategies (as proposed for instance by Feldkamp).

An advantage of the three-dimensional CBCT image is that it represents the soft tissue parts and therefore allows to register a three-dimensional CBCT image with respect to the three-dimensional image which was used for planning and which is described by the pre-data and which is referred to as herein pre-image (as will be explained in more detail later). The planning is performed based on the pre-image. The planning results in a planned relative bone position of the bony structure relative to the planned relative arrangement. Thus, the three-dimensional CBCT image allows to align the bony structure with the planned relative bone position and/or to confirm that the bony structure is already in the planned relative bony position. In particular, the bony structure has relative position relative to the treatment body part. Alternatively or additionally, the planning results in a planned relative tissue position of the (soft tissue) treatment body part relative to the arrangement. Thus, the three-dimensional CBCT image allows to align the treatment body part with the planned relative tissue position and/or to confirm that the treatment body part is already in the planned relative tissue position. Thus, the alignment results in that the treatment body part and/or the bony structure is in an aligned position which corresponds to the planned position. The alignment is in particular performed (just) before the treatment starts.

However, after the alignment, a patient can perform movements which result in a displacement of the treatment body part so that the treatment body part is no longer in the aligned position during the treatment. According to an aspect of the present invention the bone change is used as an indicator for such a movement. To determine this bone change, preferably, the CBCT image and an x-ray image is used as described below.

There are radiotherapy systems which allow to repeatedly generate three-dimensional CBCT images or just two-dimensional x-ray images during a treatment session. This allows to compare the resulting three-dimensional images or the resulting two-dimensional images with the planning data (pre-data which describe the pre-image). The comparison is aimed to determine if the treatment body part is still aligned with the planned position of the treatment body part referred to as planned relative tissue position or is displaced with respect to the planned relative tissue position. The solution of the inventors allows to use the same type of radiotherapy system, however in a different manner as will be described in the following:

Preferably, x-ray image data are provided (in particular during treatment with a treatment beam) which describe at least one two-dimensional x-ray image of the anatomical structure (which includes the treatment body part). The at least one two-dimensional x-ray image represents the bony structure included in the anatomical structure (represented by the at least one two-dimensional x-ray image). The x-ray image data (and thus the at least one two-dimensional x-ray image) is generated after the three-dimensional CBCT image, i.e. at a point in time referred to as monitoring time. This monitoring time is in particular during the treatment and in particular after the alignment while the pre-alignment time (when the three-dimensional CBCT image was generated) is in particular before the treatment and in particular before the alignment of the anatomical body part and in particular before the monitoring time. The term "before" means in particular "at least 1 s or 10 s or 1 min or 10 min before" and/or in particular "at most 1 h or 10 h or 1 day before". The term "after" means in particular "at least 1 s or 10 s or 1 min or 10 min after" and/or in particular "at most 1 h or 10 h or 1 day after".

The x-rays which generate the two-dimensional x-ray image and in particular an x-ray device (which includes an x-ray source and an x-ray detector) has a particular (known) relative position relative to the treatment device and thus relative to the actual arrangement. Since the position of the x-ray device relative to one or more possible positions (in particular orientations) of the x-ray source and the x-ray detectors is known, the one or more positions of the x-ray source and x-ray detector is known. This one or more positions represent an example for describing information on the position of an imaging geometry and on the imaging geometry itself given when generating the two-dimensional x-ray image. Preferably x-ray geometry data describe this information. Preferably, x-ray data include the x-ray image data and the x-ray geometry data.

The x-ray geometry data preferably comprises information which allows the analysis image (x-ray image) to be calculated, given a known relative position between the imaging geometry and the analysis object (anatomical body part) to be analyzed by the x-ray radiation, if the object (anatomical body part) to be analyzed is known, wherein "known" means that the spatial geometry (size and shape) of the analysis object is known. This preferably means in particular that three-dimensional, "spatially resolved" information concerning the interaction between the analysis object (anatomical body part) and the analysis radiation (x-ray radiation) is known, wherein "interaction" means for example that the analysis radiation are blocked or partially or completely allowed to pass by the analysis object. The position, in particular orientation of the imaging geometry is in particular defined by the position of the (analysis apparatus) x-ray device, in particular by the position of the x-ray source and the x-ray detection and/or in particular by the position of the multiplicity (manifold) of x-ray beams which pass through the analysis object and which are detected by the x-ray detector. The imaging geometry describes in particular the geometry (size and/or shape) of this multiplicity (manifold). The shape is for instance a conus shape with a specific angle of inclination of the side walls of the conus with respect to a central line of the conus. The position of the imaging geometry (in particular the orientation) is in particular representable by the position of a x-ray beam being and passing through the center of this multiplicity and/or by a position of a geometric object (like a truncated conus) which represents the geometry of the multiplicity (manifold) of x-ray beams. Information concerning the above-mentioned interaction is preferably three-dimensionally known, for example from a three-dimensional CT, and describes the interaction in a spatially resolved way for (in particular all of the) points and/or regions of the analysis object. Knowledge of the imaging geometry (and of its position) in particular allows a position of a source of the radiation (for example, an x-ray source) to be calculated relative to an image plane (for example plane of an x-ray detector). With respect to the connection between three-dimensional analysis objects and two-dimensional analysis images, as defined by the imaging geometry, reference is made in particular to the following publications:

1. "An Efficient and Accurate Camera Calibration Technique for 3D Machine Vision", Roger Y. Tsai, Proceedings of IEEE Conference on Computer Vision and Pattern Recognition. Miami Beach, FLUID, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Vol. RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery"
4. EP 08 156 293.6
5. U.S. 61/054,187

Preferably, x-ray image data are provided. The x-ray image data describe at least one two-dimensional x-ray image of the bony structure. In particular, the x-ray image describes the anatomical structure which includes the bony structure. The x-ray image data are generated at the monitoring time. The x-ray image data describe in particular information (i.e. include information) on the position of the bony structure relative to the actual arrangement. In more general terms, the preferably x-ray data are provided which at least include the aforementioned x-ray image data.

Preferably, the x-ray data describe information (i.e. include information) on the position of the bony structure relative to the actual arrangement. The monitoring bone position is the relative position between the bony structure and the position of the actual arrangement at a point in time (in particular during treatment) at which a monitoring of the position is performed by means of an x-ray device which generates at least one two-dimensional x-ray image. Preferably, at least two two-dimensional x-ray images from at least two different positions (i.e. two different positions of the x-ray imaging geometries) are generated. The x-ray data preferably include at least the x-ray image data and can additionally include the x-ray geometry data. Preferably, the x-ray image data and the x-ray geometry data describe together the information on the monitoring bone position. Preferably, the bone change is the change of a relative position between the monitoring bone position and the reference position.

Preferably, the x-ray image data describe at least two two-dimensional x-ray images (in particular stereoscopic images) which allow the determination of a position of bony structure (shown in the x-ray images) for instance based on the x-ray geometry data. However, even in case of just one x-ray image, the position of the bony structure can be determined as described in the following.

In particular based on the at least two different x-ray geometries given when generating the at least two different x-ray images and based on the at least two different x-ray images, the position of the bony structure is determined relative to the actual arrangement at the monitoring time. In particular, additional information on the scaling of the x-ray image is available. That is in particular from the size of the bony structure displayed by the image, the actual size of the bony structure can be inferred if the position of the bony structure relative to the x-ray imaging geometry and/or x-ray device (in particular the distance to the x-ray source and/or x-ray detector) is known, the actual size being e.g. the size as represented by the pre-image. That is, based on the size of the bony structure represented (displayed) by the two-dimensional image and based on the known actual size of the bony structure (as for instance described by the pre-image), the position of the bony structure with respect to the x-ray imaging geometry can be inferred even from just one x-ray image.

According to an embodiment, the above-mentioned x-ray geometry data are provided. The x-ray geometry data can be included in the x-ray data. The x-ray geometry data can be received, e.g. from a data base. These x-ray geometry data describe a positional relationship between the arrangement (of at least one beam position) and the imaging geometry. In particular more than one (for instance two) x-ray images can be generated and/or there are in particular different imaging geometries given when generating the more than one x-ray images. In particular, an imaging geometry is assigned to each one of the more than one x-ray images so that there is more than one imaging geometry. Thus, there is at least one imaging geometry which respectively corresponds to at least one x-ray image.

According to an embodiment, the x-ray geometry data are provided by determining the x-ray geometry data based on two x-ray images and a CBCT image generated from the same body (for instance patient or specimen) at the same location, in particular generated at the same time. Rendering DRRs from the three-dimensional CBCT image allows to determine the two x-ray image geometries of the respective two x-ray images generated by two x-ray devices, respectively. The generation of at least one x-ray image (preferably of at least two x-ray images) for providing the x-ray geometry data can be performed at the pre-alignment time. If then at the monitoring time, the at least one x-ray image (preferably at least two x-ray images) are generated, then the change of position of the three-dimensional CBCT image (generated at the pre-alignment time) is determined which is necessary in order to achieve a match of at least DRR (preferably of at least two DRRs) with the at least one x-ray image (preferably at least two x-ray images) generated at the monitoring time. The change of position of the CBCT image represents the change of position of the bony structure. This change of position is preferably described relative to the reference position. The generation of DRRs is addressed later in connection with an alternative method of determining the change of the position between the bony structure at the monitoring time and the reference position based on the CBCT image data and the CBCT position data.

Preferably, planning data are provided which describe in particular the planned relative bone position between the bony structure and the planned arrangement. The planning data are in particular generated based on pre-data which are for instance CT data or MRI data. The CT data describe a three-dimensional CT image of the anatomical structure. The MRI data describe a three-dimensional MRI of the anatomical structure. The pre-data are generated before the patient is positioned in the pre-alignment position. In particular, there is no known link between the position of the patient when generating the pre-data and when generating the CBCT data. The pre-data are generated at a point in time which is referred to as herein "planning time". The planning time is before the pre-alignment time. The term "before" means here in particular "at least 10 min or 1 h or 10 h or 1 day or 10 days" and "at most 20 days or 100 days or 1 year".

According to an embodiment, the actual relative position of the treatment body part relative to the actual arrangement is determined. This position is referred to as "monitoring tissue position". This position is determined as explained below and represents the position of the treatment body part relative to the actual arrangement at the monitoring time. Preferably, the determination is based on a position referred to as "tissue-bone pre-alignment position" described by the CBCT image data. The tissue-bone pre-alignment position is the position of the treatment body part relative to the bony structure at the pre-alignment time.

A CBCT device (which can also work as the x-ray device and) which is used to generate the CBCT data (and optionally also the x-ray image data) has preferably a fixed position relative to the treatment device. Preferably, the actual arrangement has been set by means of the treatment device based on the planning data to have a fixed position relative to the treatment device. Thus, in particular, data referred to as CBCT position data are available (e.g. stored in a data base of the computer) which describe the relative position between the CBCT image and the actual arrangement, in particular between a reference system in which the CBCT image rests and the actual arrangement. In particular, the CBCT position data allow to determine if the bony structure is in the planned relative position (aligned position) at the time of generating the CBCT image, i.e. at the pre-alignment time. A controlled change, in particular a correction of the position of the treatment body part and/or of the bony structure can be performed if this is not the case If there is a controlled change (alignment) of position of the anatomical structure, in particular the bony structure, the new position of the bony structure (after the change) is referred to as herein alignment bone position or just "changed position". According to an embodiment, the alignment bone position is the reference position. The new position of the bony structure is in particular described as a relative position between the bony structure and the actual arrangement. Preferably, position alignment data (also referred to as position change data) are provided which describe the alignment (change) of the position of the anatomical structures, in particular of the bony structure.

According to another embodiment, the reference position is the position of the actual arrangement. That is the bone reference position is the monitoring bone position.

According to an embodiment, the monitoring bone position is determined based on the x-ray data, in particular based on the x-ray image data. Furthermore, the tissue bone pre-alignment position (i.e. the relative position between the bony structure and the treatment body part) can be determined based on the CBCT image data. In particular, the bone CBCT position is determined based on the CBCT position data and the CBCT image data. The monitoring tissue position can be determined (calculated) based on the CBCT image data, the CBCT position data and the x-ray data under the assumption that the relative position between the treatment body part and the bony structure has not changed from the pre-alignment time to the monitoring time. To this end, preferably also the x-ray geometry data can be used.

According to another embodiment, the monitoring bone position is determined based on the x-ray data and additionally based on CBCT position data describing the relative position between the CBCT image (and/or the anatomical structure represented by the CBCT image) and the actual arrangement. Based on the CBCT data and the CBCT position data and in particular based on the segmentation data, a position referred to as bone CBCT position is determined. The bone CBCT position describes the relative position between the bony structure and the actual arrangement. The segmentation data describe the position of the bony structure within the CBCT image. Furthermore, the at least one x-ray image is matched, in particular registered with respect to the CBCT image. In order to achieve this, the CBCT image has to be transformed, i.e. has to undergo a translatorical and/or rotatorical transformation. The transformation is determined based on a relative position between the imaging geometry of the x-ray device present when generating the at least one x-ray image and the position of the CBCT image. The relative position being described by data referred to as CBCT x-ray data. The relative position can be for instance determined by using a model visible in both the CBCT and the at least one x-ray image and by generating x-ray images and a CBCT image from this model and by using the known structure and/or geometry of this model (which can be a cube). The relative position can also be determined by using an irregular model or just the bony structure of the patient and by detecting markers attached to the x-ray device by means of a navigation system. The latter solution is described in EP 2 119 397 or U.S. Pat. No. 7,922,391 of the present applicant which is herewith incorporated by reference. Based on this transformation, the monitoring bone position is determined. The monitoring bone position is determined based on the change of position described by the transformation and based on the bone CBCT position.

As described above, preferably at least one of x-ray geometry data and/or CBCT position data are provided in order to determine the monitoring bone position. Thus, the x-ray data which describe information on the monitoring bone position can include just the x-ray image data or the x-ray image data and the x-ray geometry data. If they only include the x-ray image data, at least then preferably the CBCT position data are provided for determination of the monitoring bone position. According to a further embodiment, both the x-ray geometry data and the CBCT position data are provided. In particular in the latter case, it is possible to determine the monitoring bone position in two different ways which allows for a checking of the reliability of the determination. Preferably at least one of the x-ray geometry data and the CBCT position data are provided for determining the bone change and/or the monitoring bone position. As a general term for the CBCT position data and the x-ray geometry data, the term "imaging position data" is used herein. That is the imaging position data comprise at least one of the CBCT position data and the x-ray geometry data.

According to an embodiment, the monitoring bone position is determined based on the CBCT image data, the x-ray geometry data and the x-ray image data (in particular without using the CBCT position data). To this end, the CBCT image undergoes a virtual translatorical and/or rotatorical transformation relative to the position of the at least one x-ray imaging geometry so that a virtual generation (DRR-generation) of the at least one x-ray image (preferably two x-ray images) is achieved in which the bony structure has the same position as in the actual at least one x-ray image. Then, the transformed CBCT image has a defined position and thus the bony structure within the CBCT image has a defined position which is the monitoring bone position. To determine the monitoring bone position, preferably the position of the bony structure within the CBCT image (preferably described by the CBCT image data) is used. In order to determine the position of the transformed CBCT image, in particular DRRs can be generated from the CBCT image and compared, in particular matched with the at least one (preferably at least two) x-ray images. The concept of DRRs is described in more detail below.

According to an embodiment, the step of providing CBCT position data is implemented by providing the x-ray geometry data and the above-mentioned CBCT x-ray data. In particular, the step of providing CBCT position data includes the step of determining the CBCT position data based on the CBCT x-ray data and the x-ray geometry data.

Preferably, the patient is already placed with respect to the treatment device at the pre-alignment time. In particular, only a smaller movement of the patient with respect to the treatment device is necessary after the pre-alignment time in order to align the bony structure and/or the treatment body part with respect to the actual arrangement based on the CBCT data. Thus, it is unlikely that there is a major shift between soft tissue structures like the treatment body part and the bony structure.

According to a preferred embodiment, the monitoring bone position is determined by generating digitally reconstructed radiographs (referred to as "DRRs") from the three-dimensional CBCT image. Preferably, at least one two-dimensional DRR is determined which matches the at least one two-dimensional x-ray image. In order to generate the DRRs, imaging geometries are simulated. If a "DRR" matches an x-ray image, the simulated imaging geometry (used to generate the DRR) is referred to as matching imaging geometry. To each of the at least one two-dimensional x-ray image corresponds a respective matching imaging geometry. The matching of a DRR with an x-ray image is preferably performed based on (in particular only based on or predominantly based on) the bony structure such that the bony structure shown in the DRR and shown in the x-ray image match with each other, in particular achieve a best match. In particular, other parts of the anatomical structure which are not part of the bony structure are weighed less in the matching process than the bony structure. In particular, a segmented bony structure is used for matching, in particular only the bony structure is used for matching. Preferably, there are at least two x-ray images which are respectively to be matched with one of the simulated DRRs. Preferably, a plurality of DRRs are generated and the matching DRRs are selected out of the plurality of DRRs.

Due to the simulation, the relative position (in particular orientation) between the at least one matching imaging geometry and the anatomical structure (in particular bony structure) represented by the three-dimensional CBCT image is known. If assuming that the three-dimensional image adopts virtually the same position in space as the anatomical structure (which it represents and which includes the bony structure), it can also be said that the relative position between the at least one matching imaging geometry and the three-dimensional CBCT image is known due to the simulation. Based on the relative position between the (at least one) matching imaging geometry and the anatomical structure (three-dimensional CBCT image) and the (known) relative position between the position of the anatomical structure (three-dimensional CBCT image) and the position of the actual arrangement (at the pre-alignment time), the relative position between the matching imaging geometry and the actual arrangement at the pre-alignment time can be determined. In case this relative position differs from the relative position between the (at least one) x-ray imaging geometry and the actual arrangement at the monitoring time, this is due to a positional change of the anatomical structure. This positional change corresponds to an imaging geometry difference which will be explained in the following.

If there had been a positional change (e.g. rotational and/or translatoric change) of the bony structure from the pre-alignment time to the monitoring time, the position of the at least one x-ray imaging geometry relative to the actual arrangement at the monitoring time will differ from the corresponding at least one position of the at least one matching imaging geometry relative to the position of the actual arrangement at the pre-alignment time. This difference is the above-mentioned imaging geometry difference. Thus, to each of the at least one x-ray imaging geometries corresponds one imaging geometry difference. The imaging geometry difference represents the positional change of the bony structure (in particular in case the bony structure was used for the above-mentioned matching process). The image geometry difference, in particular the positional change can be zero or larger than zero.

In particular, the at least one image geometry difference describes the positional change of the bony structure relative to the actual arrangement from the pre-alignment time to the monitoring time.

According to an embodiment, the monitoring bone position can be determined by determining the positional change of the anatomical structure represented by the CBCT image from the pre-alignment time to the monitoring time relative to the position of the actual arrangement. Thus, in other words, according to the latter embodiment, a new position of the bony structure and thus of the three-dimensional CBCT image (which represent this bony structure) relative to the position of the actual arrangement is determined based on the at least one image geometry difference. As mentioned above, the three-dimensional CBCT image is assumed herein to have a (virtual) spatial position which is identical with the spatial position of the anatomical structure which it represents. The position of the bony structure within the newly positioned anatomical structure and thus within the three-dimensional (CBCT image (referred to as new CBCT image) and relative to the position of the actual arrangement represents the monitoring bone position (if the reference position is in accordance with an embodiment identical with the position of the actual arrangement). The newly positioned anatomical structure is in particular assumed to be identical (rigid property) with the anatomical structure represented by the three-dimensional CBCT image (also referred to as shortly "CBCT image") at the pre-alignment time, however, the newly positioned anatomical structure and thus the new CBCT image can have a position (relative to the actual arrangement) which is different from the position of the anatomical structure (and thus of the CBCT image) at the pre-alignment time. As mentioned above, the monitoring bone position is preferably determined based on the position of the bony structure within the newly positioned anatomical structure and based on the relative position between the newly positioned anatomical structure and the reference position which is for instance the position of the actual arrangement.

The position of the bony structure within the anatomical structure and thus within the CBCT image at the pre-alignment time is preferably described by using segmentation data. The segmentation data describe in particular the relative position between the segmented bony structure and the anatomical structure and thus the position of the bony structure within the CBCT image. This relative position is referred to as herein segmented bone position. Thus, the bone CBCT position can be determined based on the segmented bone position (e.g. represented by a first vector) and the relative position between the CBCT image and the actual arrangement (e.g. represented by a second vector), e.g. by adding vectors representing the relative positions (e.g. by adding the first and second vector). The segmentation data describe the segmented bone position, for instance in a reference system in which the anatomical structure and the CBCT image is at rest. The segmentation data can for instance be generated by a (non-rigid) matching of a three-dimensional (in particular segmented) pre-image (for instance a CT image) with the CBCT image. The pre-image is in particular used for planning and the bony structure is identified (in particular segmented) during the planning process which is performed based on the pre-image.

The segmentation data describe in particular further the relative position between the segmented treatment body part and the bony structure. This relative position is referred to as tissue-bone pre-alignment position. This tissue-bone pre-alignment position can be used to update the planned relative bone position based on the CBCT image data and the CBCT position data. If for instance the relative position between the bony structure and the treatment body part has changed between the planning time and pre-alignment time, then preferably also the planned relative bone position is changed (updated) accordingly. Preferably, the updated planned relative bone position is such that after the alignment of the bony structure with the updated planned relative bone position, the position of the treatment body part relative to the actual arrangement corresponds to the planned relative tissue position (if the relative position between the bony structure and the actual arrangement corresponds to the new (updated) planned relative bone position). The relative position between the treatment body part and the bony structure is referred to as tissue-bone pre-alignment position. Thus, the updated planned relative bone position can be determined (and in particular indicated to a user as a proposal or automatically set) based on the tissue-bone pre-alignment position and the planned relative tissue position. As mentioned above, the reference position can be the updated relative bone position or the original relative bone position (in particular depending on the preference of the user). According to another embodiment, the user sets the updated planned relative bone position in accordance with his preferences.

In the previous embodiment described above, the monitoring bone position is determined by generating DRRs and by matching (in particular registering) the DRRs with the two-dimensional x-ray images. This is also possible according to another embodiment. According to this another embodiment which can be combined with the previous embodiment, the monitoring bone position is determined based on the x-ray data without the above described matching of DRRs. For instance several x-ray images are generated from different orientations and the x-ray imaging geometry (given when generating these x-ray images) is known by the x-ray geometry data. Then, the monitoring bone position can be determined based on the x-ray data. For instance, the x-ray images (corresponding to different x-ray imaging geometries) are displayed on a screen and data referred to as bony structure data are received by the method. The bony structure data describe the position and/or geometry of the at least part of the bony structure in at least one of the x-ray images. For instance an operator or a pattern recognition algorithm identifies at least a part of the bony structure on the screen by means of a mouse or a pen for generating the bony structure data. Based on the received bony structure data, then the monitoring bone position is determined. Furthermore, under the assumption that the tissue-bone pre-alignment position is not changed from the pre-alignment time to the monitoring time, the monitoring tissue position can be determined based on the monitoring bone position determined in the previous step. The monitoring bone position represents the position of the bony structure. Furthermore, the tissue-bone pre-alignment position (described by the CBCT data) describe the relative position between the treatment body part and the bony structure For instance, the bony structure data describe the position of one or more particular bone elements (e.g. landmarks) part in the at least one x-ray image and the tissue-bone pre-alignment position describers the relative position of the treatment body part and the one or more particular bone element. Furthermore, based on the x-ray geometry data and the position of the one or more particular bone elements (e.g. landmarks) in one or more of the x-ray images, the position of the one or more particular bone elements relative to the arrangement (i.e. the monitoring bone position) can be determined. (In particular, based on the monitoring bone position and the set tissue-bone monitoring position, the monitoring tissue position can be determined.)

As can be seen from the above, the bone change and/or the monitoring bone position can be determined by determining the monitoring bone position based on the x-ray image data and the x-ray geometry data and/or by determining the bone change by using the reference position which can be determined based on the CBCT image data and the CBCT position data (if for instance the reference position is the alignment bone position or the bone CBCT position). However, as explained above it is also possible to use both the CBCT image data and the x-ray image data in addition to the imaging position data in order to determine the monitoring bone position. The imaging position data can comprise the CBCT position data and/or the x-ray geometry data. According to an advantageous aspect of the present invention both the CBCT image data and the x-ray image data are used for determining the bone change and/or the monitoring bone position while different intermediate steps can result in this determination.

In particular, the aforementioned segmentation data describe the tissue-bone pre-alignment position. As mentioned before, the segmentation data can be generated during planning and by matching the "segmented" pre-image with the CBCT image.

As mentioned above, the segmentation data can be determined based on the pre-data and the CBCT data. The tissue-bone pre-alignment position and/or bone CBCT position (and/or bone alignment position) can be determined automatically based on the segmentation data. Alternatively or additionally, the tissue-bone pre-alignment position and/or the segmented bone position can be received by the data processing method. In particular, the data processing method outputs the CBCT image (for instance on a screen) and an operator indicates the position of the bony structure (and optionally the position of the treatment body part). The indicated position (or positions) is (or are) received by the data processing method and describe the segmented bone position (and optionally the tissue-bone pre-alignment position). The provided segmented bone position is preferably used to determine the monitoring bone position (as mentioned above).

As mentioned before, according to an advantageous embodiment, the segmentation data are provided. This segmentation data can be generated during a planning process. The planning process results in particular in planning data which describe the planned relative bone position. According to a preferred embodiment, providing the planning data represents a further step of the data processing method. The step of providing planning data is in particular a receiving step. The provision of the planning data enables the data processing method to determine the monitoring bone position if the reference position is the planned relative bone position.

According to an embodiment, the segmentation data describe the segmented bony structure in the CBCT image. This can be done for instance by an automatic segmentation algorithm or by means of a user which identifies the bony structure in the CBCT image. In this way, the segmentation data describe in particular a three-dimensional model of the bony structure. This three-dimensional model of the bony structure (based on the CBCT image) is then preferably matched, in particular registered with respect to the at least one x-ray image. Since there is a defined positional relationship between the three-dimensional model of the bony structure and the CBCT image, the new position of the anatomical structure and thus of the three-dimensional CBCT image relative to the actual arrangement can be determined since the relative position between the three-dimensional model and the actual arrangement is known due to the above described matching (in particular registration) step. In particular, the x-ray geometry data can be used to determine the position of the (registered) three-dimensional model. The registered three-dimensional model has a position in the virtual space which results in the at least one (preferably at least two) x-ray images if the at least one x-ray image is generated in accordance with the x-ray imaging geometry which has a position as described by the x-ray image geometry data. Thus, the position of the bony structure can be determined just based on the CBCT image data, the x-ray image data and the x-ray geometry data. Alternatively, the position of the (registered) three-dimensional model can be determined based on the position of the CBCT image (described by the CBCT position data) and the virtual movement of the CBCT image which was necessary to achieve the registration as well as based on the position of the three-dimensional model within the CBCT image. The monitoring bone position can then be determined based on the position of the bony structure (segmented bone position) within the registered (newly positioned) anatomical structure and based on the relative position of the registered (newly positioned) anatomical structure relative to the reference position, in particular relative to the position of the actual arrangement.

The above-mentioned embodiment is a feature-based embodiment, i.e. the matching, in particular registration process is based on features of the three-dimensional CBCT image, in particular based on features of the bony structure (in particular its geometry, i.e. size and/or shape). Instead of the three-dimensional model which represent the bony structure it is also possible to use two-dimensional models of the bony structure which represent a surface of the bony structure. Then the two-dimensional model of the bony structure is matched, in particular registered with respect to one-dimensional features, in particular contours (outlines) of the bony structure represented by the x-ray image. Thus, generally a model (in particular three-dimensional or two-dimensional model) of the bony structure is generated from the CBCT image which in particular represents at least a part of two- and/or three-dimensional features (in particular geometry features) of the bony structure. Based on this model a matching, in particular registration process is performed with respect to the two- and/or one-dimensional features of the x-ray image. Based on the registered model, the monitoring bone position can be determined. This determination is in particular performed by determining the position of the CBCT image based on the position of the matched (registered) model. As described above, the monitoring bone position can be determined based on the two-dimensional geometry of the bony structure described by the at least one x-ray image and the three-dimensional geometry of the bony structure described by the CBCT image.

As mentioned above, the planning data are preferably provided based on the pre-image. The pre-image is described by the pre-data. The pre-image represents a three-dimensional image of the anatomical structure which includes the treatment body part. The pre-data are generated before generating the CBCT-data. In particular, a spatial relationship between the pre-image and the actual arrangement is unknown (i.e. not provided to the data processing method). However, as mentioned above, preferably the planning data describe the relative position between the pre-image and the planned arrangement, in particular the planned relative position between the bony structure identified (in particular segmented) in the pre-image relative to the planned arrangement. In accordance with an advantageous embodiment, the data processing method controls the position of the bony structure so that an actual position between the bony structure and the actual arrangement becomes identical with the planned relative bone position. The control is performed based on the determined change in the bone reference position. In particular, if there is a deviation between the monitoring bone position and the planned relative bone position, a control is performed in order to change the actual relative position and to reduce, in particular to minimize, in particular to zero this deviation.

As mentioned above, a patient is preferably first analyzed in order to generate the pre-data (e.g. by using a CT or MRI). The generation of the pre-data can be on a different day and in particular in a different room so there is in particular no known spatial relationship between the reference system in which the pre-image is described and the position of the actual arrangement. The position of the actual arrangement is set relative to a patient placed relative to the treatment device within the treatment system (for instance on a couch of the treatment system). The placement is in particular performed by a medical staff member who tries to align the patient in accordance with the planning, in particular based on landmarks visible on the body of the patient. Since generally the treatment body part is inside the patient, the member of the medical staff is not aware if the placement is correct. Therefore, preferably, the abovementioned three-dimensional CBCT images are generated after the placement (pre-alignment) of the patient with respect to the treatment device at the pre-alignment time. Preferably, the relative position between a reference system within which the actual arrangement is set and a reference system within, which the three-dimensional CBCT image is described, is known. Thus, preferably the CBCT position data are provided to the method according to an embodiment of the invention. The CBCT position data describes the relative position between the three-dimensional CBCT image and the actual arrangement at the time of generating the CBCT image, i.e. at the pre-alignment time. This position is referred to as pre-alignment CBCT position. Since the anatomical structure is described by the CBCT image, the CBCT position data also describe the relative position between the anatomical structure and the actual arrangement at the time of generating the CBCT image. Preferably, based on the pre-alignment CBCT position (described by the CBCT position data) and based on the segmented bone position described by the segmentation data, the bone CBCT position is determined. The bone CBCT position is the relative position between the bony structure and the actual arrangement at the pre-alignment time. Performing an alignment between the pre-alignment time and the alignment time (in particular at the alignment time) is an optimal and preferred but not an obligatory step.

Preferably, the three-dimensional CBCT image and the three-dimensional pre-image is matched in accordance with an advantageous embodiment. The matching can be performed based on (in particular only based on or predominantly based on) the treatment body part and/or the bony structure, i.e. so that the treatment body part and/or the bony structure shown in the CBCT image and the treatment body part and/or the bony structure shown in the pre-image match with each other in particular achieve a best match. In particular other parts of the anatomical structure which are not the treatment body part and/or the bony structure are weighed less in the matching process than the treatment body part and/or the bony structure. In particular, the segmented treatment body part, in particular only the segmented treatment body part is used for matching. The matching is in particular a rigid matching that is the image, in particular the segmented treatment body part is not deformable. Based on the matched images, a difference between the planned relative bone position and the bone CBCT position can be determined. This difference is referred to as pre-alignment bone difference. Alternatively or additionally, a difference between the planned relative tissue position and the pre-alignment tissue position (position of the treatment body part at the pre-alignment time) can be determined. This difference is referred to as pre-alignment tissue difference.

In particular, if there is no pre-alignment bone difference, no control (adjustment) for changing the relative position between the bony structure and the actual arrangement is performed according to an embodiment. If there is a pre-alignment bone difference, then preferably (but not obligatory) the controlled change is performed (at least in case a predefined threshold for the difference is passed). The controlled change is preferably performed based on the determined pre-alignment bone difference. Thus, in accordance with an advantageous embodiment, in dependence on the pre-alignment bone difference, control data (referred to as alignment control data) are determined. The term "in dependence on" means in particular that this control is performed if there is a difference in particular if the difference is above a predetermined threshold (which can be zero or more) and means in particular that in case of the controlled change the control is based on the determined pre-alignment difference. According to an alternative embodiment, the controlled change (adjustment) is performed to compensate the pre-alignment tissue difference.

The determined alignment control data are for controlling the actual relative bone position. Preferably, the controlled change is performed such that the difference between the planned relative bone position and the actual relative bone position after the control is smaller than the pre-alignment difference, in particular so that the pre-alignment bone difference is zero. In particular, the alignment control data are constituted to control the actual relative bone position to correspond to the planned relative bone position. Preferably, according to an advantageous embodiment, the alignment control data are outputted in order to achieve the control before the monitoring time, in particular before the treatment of the treatment body part by means of the treatment beam starts. In particular, at the monitoring time, it is assumed that the position of the bony structure has been (already) controlled in accordance with the alignment control data. The position of the bony structure after the alignment is the alignment bone position. The alignment of the bony structure relative to the actual arrangement describes in particular a change (referred to as alignment change) of the relative position between the bony structure and the actual arrangement and is in particular described by data referred to as position alignment data. The position alignment data are preferably determined based on the alignment control data. In particular, to this end the alignment change is deemed to correspond to the controlled change.

According to a further advantageous embodiment, control data (referred to as x-ray based control data) are determined. These control data are for controlling the position of the bony structure based on the x-ray data. In particular in case the determined bone change is more than a predetermined threshold, the x-ray based control data are determined, in particular output to control the position of the treatment body part.

According to the above-described advantageous embodiments, data (referred to as alignment CBCT position data) are provided. The alignment CBCT position data describe the relative position between the three-dimensional CBCT image and the actual arrangement at a point in time referred to as alignment time. This position is referred to as CBCT alignment position since it preferably relates to the position after the aforementioned alignment is performed based on the CBCT image. That is, in other words, the alignment CBCT position is in particular the relative position between the anatomical structure and the actual arrangement after outputting the alignment control data and after performing the controlled change (alignment) of position of the anatomical structure. In particular, the alignment bone position is the position of the bony structure relative to the actual arrangement at a point in time (the alignment time) before the monitoring time and after the pre-alignment time, in particular after controlling the position of the anatomical structure in accordance with the alignment control data. In particular, there is an extended time difference between the alignment time and the monitoring time which can result in the change of the bone reference position, for instance due to an (unintended) movement of the patient or due to vital functions of the patient (breathing, heart beat).

The alignment CBCT position data can be determined on the basis of position change data. According to an embodiment, the position change data describe a positional displacement of the anatomical structure (in particular of the bony structure) which in particular corresponds to a compensation of the determined pre-alignment bone difference or pre-alignment tissue difference (in case the alignment control data are determined to result in a fully compensated pre-alignment bone difference or pre-alignment tissue difference) and based on the pre-alignment position data described above. The aforementioned position alignment data preferably correspond to the position change data, in particular they are identical.

Advantageously, a difference (referred to as correction difference) is determined which represents the bone change. Preferably control data (referred to as x-ray based position control data) are determined in dependence on the determined correction difference. The x-ray based position control data are for controlling the relative position between the actual arrangement and the bony structure so that the correction difference is compensated.

The above-mentioned term "in dependence on the correction difference" means in particular that the x-ray based position control data are determined and/or outputted only if the correction difference exceeds a predetermined threshold. This threshold can be zero or can be above zero. The term "in dependence on" means in particular that the correction difference is only determined and/or only outputted if the difference is above zero.

Advantageously the method comprising a step of generating control data (referred to as x-ray imaging control data) which are constituted to cause the generation of the x-ray data (in particular of the x-ray image data) after a (regular or irregular) period of time or in response to an external signal. In particular during this period of time, there is a treatment of the treatment body part by the treatment beam.

Preferably the generation of the x-ray images is repeated and the output of the x-ray based position control data is also repeated. In particular outputting the x-ray imaging control data and outputting the x-ray based position control data are repeated. In particular, the x-ray based position control data are determined based on the lastly determined bone change and/or monitoring bone position (which was determined based on the lastly received x-ray image data). These steps are in particular repeated during treatment of the treatment body part in particular with the aim to (repeatedly) correct the position of the treatment body part positioning order to compensate the bone change determined based on the lastly received x-ray image data. As mentioned above, the generation of the x-ray images can be repeated. Each time the generation is repeated, the bony structure has a particular position relative to the reference position. This particular position is also referred to as previous monitoring bone position if it is the position of the bony structure before the monitoring time. According to an embodiment, the reference position is chosen to be one of the particular positions (previous monitoring bone positions). The particular position based on the lastly (most recently) received x-ray image data is referred to as last monitoring bone position and the particular position determined based on the x-ray image data received directly preceding the lastly received x-ray image data is referred to as preceding monitoring bone position. According to an embodiment, the reference position is set to be the preceding monitoring bone position. In particular the bone change is determined by comparing the last monitoring bone position with the preceding monitoring bone position. According to an embodiment, the bone reference position is a relative position between the last monitoring bone position and the preceding monitoring bone position. For determining the previous monitoring bone position, preferably previous x-ray image data are provided. The previous x-ray image data describe at least one two-dimensional x-ray image of the anatomical structure. The at least one two-dimensional x-ray image represents the bony structure and is generated at the previous monitoring time. The previous monitoring bone position is preferably determined based on the previous x-ray image data, the CBCT image data and the imaging position data.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention is also directed to radiotherapy system which comprises the above-mentioned computer. Furthermore, the radiotherapy system comprises preferably the treatment device. Preferably, the treatment system comprises a couch for placing the patient thereon. The treatment device is preferably constituted to treat the treatment part if the patient is placed on the couch for treatment. In particular, the treatment device is constituted so that the relative positions between the beam positions relative to the treatment device are controllable (in particular settable) to that an arrangement of beam positions can be set, the relative positions of the set arrangement corresponding preferably to (in particular are identical with) with the relative positions between the beam positions of the planned arrangement. In particular the couch and the treatment device are constituted so that the relative position between the set arrangement of beam positions and the treatment body part is changeable.

Preferably the treatment system comprises a CBCT-device. The CBCT-device is constituted to generate the three-dimensional CBCT images. In particular, the computer comprises a database within which the relative position between the CBCT image generated by the CBCT-device and a reference system of the treatment device is known. Preferably, the relationship between a reference system within which the actual arrangement is set and the reference system of the CBCT image is stored in the data base and/or is determinable based on the data stored in the database of the computer and based on data describing the set actual arrangement.

According to an embodiment, the x-ray images are generated by means of the CBCT-device. According to another embodiment, an x-ray device (which is independent from the CBCT-device) is part of or associated with/attached to the radiotherapy system and is used for generating the two-dimensional x-ray images. Preferably, the database of the computer stores a positional relationship between the x-ray imaging geometry (or x-ray imaging geometries) and reference system of the CBCT-image and/or a reference system within which the position of the actual arrangement is set. Preferably, after setting of the arrangement, the relative beam positions defined by the arrangement are fixed with respect to each other but, according to an embodiment, the position of set arrangement can be determined with respect to the treatment device. The actual arrangement is set in particular in accordance with control data (referred to as arrangement control data which are provided (in particular received)). The arrangement control data can be set by an operator to comply as best as possible with the planned relative position under the assumption of an assumed position of the treatment body part (after placing the patient on the couch). The arrangement control data defines a position of the actual arrangement in the reference system of the arrangement.

According to an embodiment, the position of the couch is changeable by means of the alignment control data and/or x-ray based control data. Additionally or alternatively, the position of the actual arrangement within the reference system of the arrangement is changeable based on the alignment control data and/or the x-ray based position control data. Thus, the position of the treatment body part relative to the actual arrangement can be changed by changing the position of the couch and/or by changing the position of the actual arrangement within the reference system of the treatment device.

In particular, control signals are issued by the computer to the couch and/or to the treatment device for changing the relative position between the couch and the reference system of the treatment device.

The present invention is in particular directed to the following embodiments:

A. Data processing method for use in the field of radiation therapy and for determining a difference in position of a bony structure and/or whether there is this difference, wherein an anatomical structure of a patient includes the bony structure and a treatment body part to be treated by a treatment beam of a treatment device, the data processing method being constituted to be performed by a computer and comprising the following steps:

provlding CBCT data describing a three dimensional CBCT image of a region which includes the anatomical structure, the CBCT image representing the bony structure at a time referred to as pre-alignment time;

optionally providing target position data describing a target position which is a relative position between the bony structure and an actual arrangement of at least one position of the treatment beam;

providing CBCT position data describing the relative position between the CBCT image and the actual arrangement;

determining a position referred to as bone CBCT position describing the relative position between the bony structure and the actual arrangement based on the CBCT data and the CBCT position data;

optionally, in case of a controlled change of position of the anatomical structure after generation of the CBCT image, providing position change data describing the change of position of the anatomical structure relative to the actual arrangement and determining a position referred to as changed position which describes the relative position between the bony structure and the actual arrangement based on the bone CBCT position and the change of position and;

providing x-ray data describing information on a position of the bony structure, referred to as monitoring bone position, relative to the actual arrangement at a point in time, referred to as monitoring time, the monitoring time being after the pre-alignment time;

determining a difference or whether there is a difference optionally between the monitoring bone position and the target position and/or optionally between the monitoring bone position and the changed position, in case there was a controlled change and/or between the monitoring bone position and the bone CBCT position.

B. The data processing method of the above embodiment A, wherein x-ray data are repeatedly provided at subsequent points in time and a position of the bony structure relative to the actual arrangement is repeatedly determined based on the x-ray data, the position is referred to as bony structure position and in particular the following is repeatedly performed:

determining a difference or whether there is a difference optionally between the most recently determined bony structure position and the target position and/or between the most recently determined bony structure position and a previously determined bony structure position which can also be the monitoring bone position and/or optionally between the bony structure position and the changed position, in case there was a controlled change and/or between the bone structure position and the bone CBCT position.

In particular, the method can comprise the optional step of compensating the determined difference only in case the difference between subsequent positions or difference between the previous position and the later position is above a predetermined threshold (referred to as action threshold). According to a further embodiment, an indication signal (e.g. a visual, audio and/or tactile signal) is issued in accordance with a further step of the method in case the determined difference is above the predefined threshold in particular to warn the staff members that a reposition of the patient can be necessary in order to achieve good treatment result. In particular, the generation of a further CBCT image can be initiated in case the difference is above the predefined threshold, in order to determine if the relative position between the treatment body part and the bony structure has changed.

The above-described second invention in particular uses the bony structure shown in x-ray images as an indicator for the position of the treatment body part, in particular as an indicator whether the treatment body part is still in the correct position or has left the correct position. In particular, it is assumed that the treatment body part is in the correct position relative to the actual arrangement if the bony structure position coincides with the above-mentioned target position. In particular in addition to the CBCT image, x-ray images are generated for determining a change of the bony structure position which is used as an indicator. The CBCT data are preferably used for determining this change. Thus, preferably subsequent to the CBCT image, at least one x-ray image is generated. Preferably the at least one x-ray images are repeatedly generated at later points in time in order to track any movements of the bony structure during the treatment.

In particular the above step of providing the x-ray data includes:

providing x-ray image data describing at least one two-dimensional x-ray image of the anatomical structure, the at least one two-dimensional x-ray image representing the bony structure (110) and the x-ray data being generated at a point in time (FIG. 2*d*); and providing x-ray geometry data describing a positional relationship between the actual arrangement (13) and at least one imaging geometry, referred to as x-ray imaging geometry, given for generating the at least one x-ray image, and, at least in case of only one x-ray image, describing information on a size of the represented bony structure (110) in dependence on the position of the bony structure with respect to the imaging geometry.

According to a further embodiment of the further invention, the data processing method comprises the following:

The data processing (of the further invention) as described in one of the above embodiments and comprising the following step:

determining data referred to as therapy control data in dependence on the determined difference for controlling the relative position between the actual arrangement and the bony structure so that the determined difference is compensated.

The data processing method preferably further includes the step of outputting the therapy control data in order to control the relative position between the couch and the actual arrangement.

Preferably, the therapy control data are determined and/or output each time a new x-ray data has been generated based on which the position of the bony structure relative to the actual arrangement can be determined. To this end, preferably control data referred to as x-ray imaging control data are generated which are constituted to cause the generation of the x-ray image data in particular after a period of time during which the treatment body part has been treated by the treatment beam.

The position of the bony structure can be determined in various manners based on the x-ray data and optionally based on the CBCT data and optionally also based on the CBCT position data. As described above with respect to the first invention, the three-dimensional CBCT image can be registered with respect to the at least one x-ray image. The positional change (for instance rotatorical and/or translatorical change) of the three-dimensional CBCT image in order to achieve the registration allows to determine a difference between the bone CBCT position and the monitoring bone position. Thus, based on the bone CBCT position and the determined difference, the monitoring bone position can be determined. This registration can be repeated for the different x-ray data generated repeatedly in order to repeatedly determine the bony structure position.

As mentioned with respect to the first invention, the registration can be performed based on image features by for instance generating DRRs from the CBCT image and matching those DRRs with the at least one x-ray image. According to a further embodiment, the registration can be based on features, in particular two- or three-dimensional models of the bony structure generated from the three-dimensional CBCT image. Thus, in particular the determination of the difference between the subsequent bony structure positions can be based on the image information included in the three-dimensional CBCT image or based on features of the bony structure extracted from the three-dimensional CBCT image. In particular, the above-described matching imaging geometry used with respect to the first invention can be used in order to determine the difference between the subsequent positions. Thus, the method in particular comprises the following steps:

determining at least one two-dimensional digitally reconstructed radiograph (DRR) from the three-dimensional CBCT image which matches the at least one x-ray image, the matching at least one two-dimensional digitally reconstructed radiograph (DRR) resulting from a simulation of at least one imaging geometry given for generating the at least one two-dimensional digitally reconstructed radiograph (DRR), the imaging geometry being referred to as matching imaging geometry, wherein the matching is performed based on the bony structure (110) shown in both the at least one two-dimensional digitally reconstructed radiograph (DRR) and the at least one x-ray image;

providing a relative position between the at least one matching imaging geometry and the actual arrangement.

The monitoring bone position is an example for a bony structure position.

The further invention also encompasses the following embodiment:

Data processing method for use in the field of radiation therapy and for verifying the position ($d_{4at}$) of a treatment body part (100) relative to an actual arrangement (13) of at least one position of a treatment beam issued by a treatment device (10), the position ($d_{4at}$) being referred to as monitoring tissue position and the treatment body part (100) being a soft tissue part of an anatomical structure of a patient; the data processing method being constituted to be performed by a computer (50) and comprising the following steps:

providing (S6, S7) CBCT data describing a three-dimensional CBCT image of the volume encompassing the target region, the three dimensional CBCT image including the bony structure (110) at a point in time, referred to as pre-alignment time (FIG. 2*b*);

determining a rotational and/or translational registration offset that will bring the CBCT volume and the contained structures in the correct position relative to said actual arrangement.

applying said registration offset to either the patient or the actual arrangement to modify the relative position between the patient and the actual arrangement.

providing (S11) x-ray data describing information on a position ($d_{1ba}$) of the bony structure (110), referred to as monitoring bone position ($d_{1ba}$), relative to the actual arrangement (13) at a point in time during treatment, referred to as monitoring time (FIG. 3*d*), the monitoring time being after the pre-alignment time (FIG. 2*b*);

Comparing the position of the bony structures in the registered CBCT data with the position of the bony structures in the x-ray data to establish a position difference.

Comparing said position difference with an action threshold that determines the need to reposition the patient during the treatment.

In the following detailed description of embodiments, further advantageous features are disclosed. Different features of different embodiments can be combined.

FIGS. 3a and 3b explain the steps of a method according to an embodiment of the invention.

Figure 1:
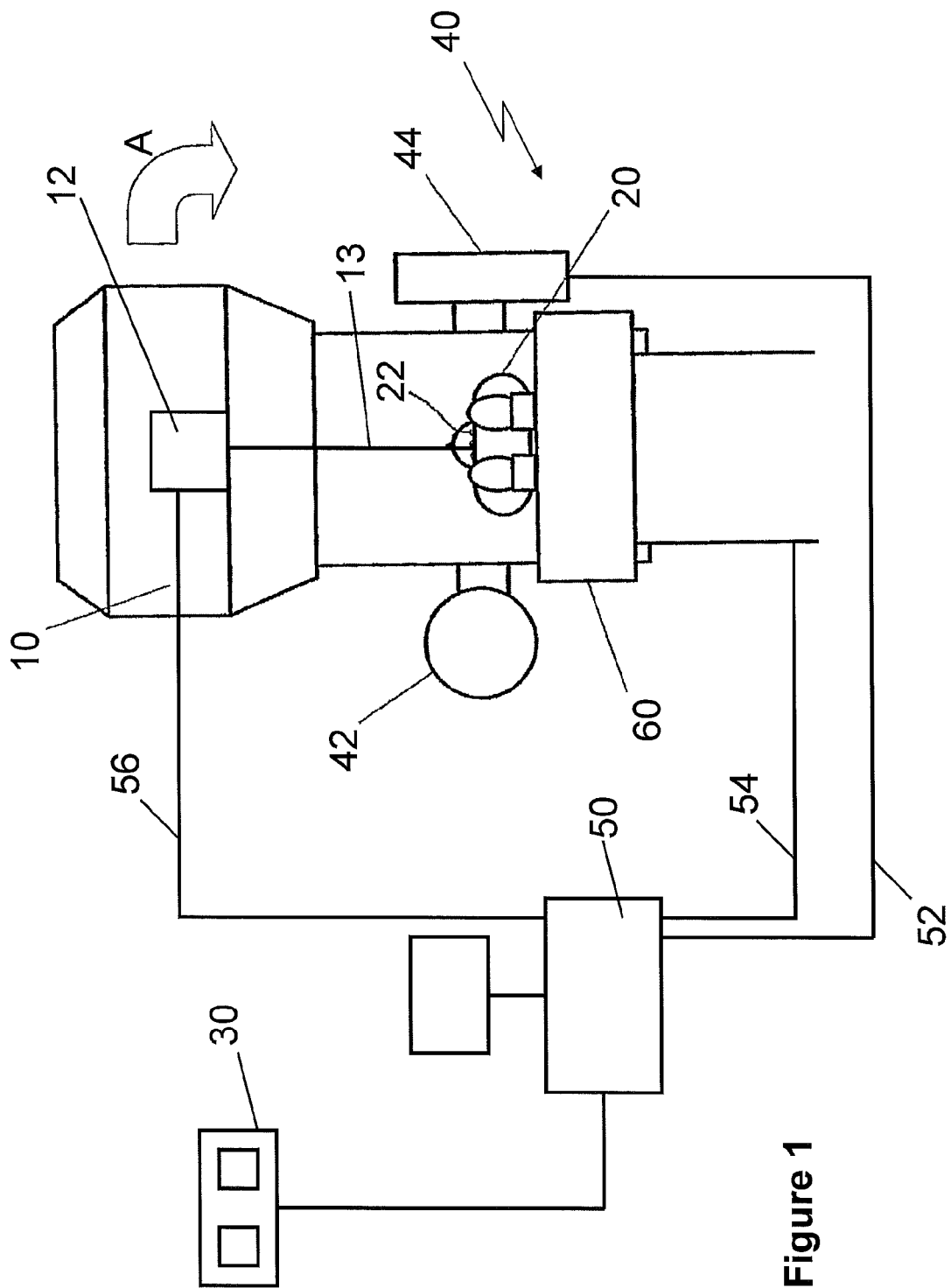
FIG. 1 shows schematically a treatment system in accordance with the invention.

FIG. 1 shows a radiotherapy system in accordance with an embodiment of the invention. A treatment device 10 includes a beam source 12 which issues a treatment beam 13 and which can be movable in a direction A relative to the treatment device 10. In the example given, the treatment device 10 has a fixed position in the room. The treatment beam 13 hits a patient 20. On the surface of the patient 20, optical markers 22 are optionally attached. The position of the optical markers 22 can be detected by means of a camera 30 of a navigation system used in image guided surgery. The camera 30 is connected with a computer 50 on which a program for image guided surgery is running in order to determine the position of the markers 22. Preferably, the patient 20 is positioned so that the determined position of the markers 22 corresponds to the planned relative position of the markers 22 and/or so that the determined positions of landmarks of the patient body correspond to the planned relative positions of the landmarks.

The radiotherapy system preferably comprises a CBCT device 40 which comprises an x-ray source 42 and an x-ray detector 44. Thus, the CBCT device 40 also works as the x-ray device used for monitoring the position of the treatment body part at the monitoring time. Preferably, the x-ray source 42 and the x-ray detector 44 are rotatable around the patient 20 in order to generate the plurality of x-ray images of the patient from different directions. Based on this plurality of the images, the CBCT image (and thus the CBCT data) is generated by the computer 50 which is connected to the detector 44 by a signal line 52. In particular, the plurality of positions of the x-ray detector 44 and x-ray source 42 (adopted during generation of the CBCT image) is known in the reference system of the CBCT image for generating the CBCT image based on this knowledge.

In particular two x-ray images from different directions are generated at the monitoring time in order to generate the x-ray image data.

Preferably, the computer 50 is constituted to control the position of a couch 60 on which the patient 20 is lying by means of a signal line 54 and the position or aiming of the treatment beam source 12 by means of a signal 56. Furthermore, the computer 50 is preferably constituted to initiate the generation of the CBCT image by means of the signal line 52 and of preferably at least two and less than five images from different directions by means of the device 40 at the monitoring time. Preferably, two stereoscopic images are generated by means of the x-ray device 40 while preferably more than 50 x-ray images are generated in order to determine the CBCT image.

Figure 2:
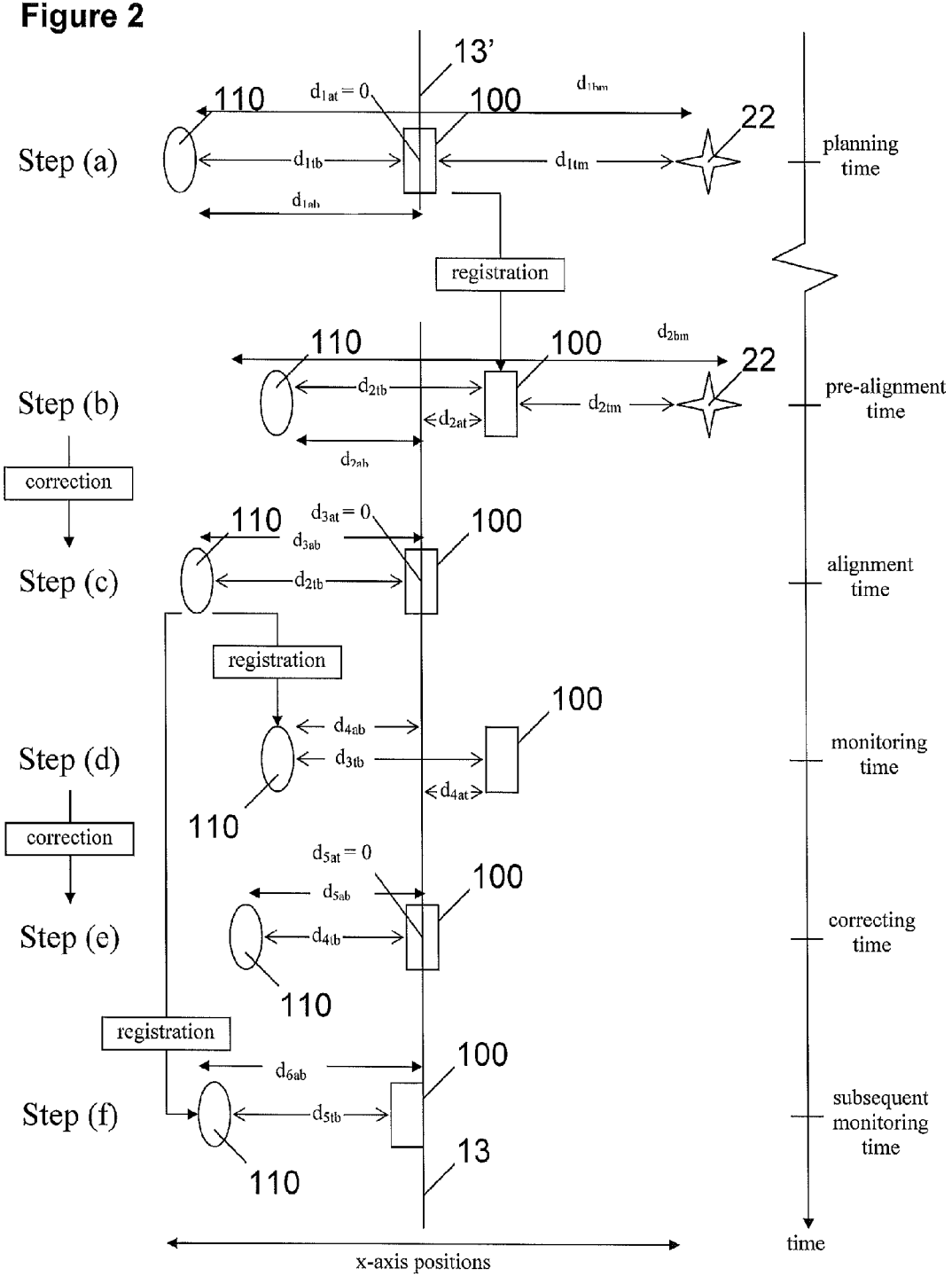
FIG. 2 shows principles of the determination and correction of the position of the treatment body part.

FIG. 2 shows different steps before and during treatment of a patient with a treatment beam in a schematic one-dimensional manner. FIG. 2a shows a treatment body part 100 in a rectangular shape and a bony structure 110 in a round shape in different positions along an x-axis of a first reference system (step a)) in which the planned arrangement is at rest and a second reference system (steps b) to f)) in which the actual arrangement is at rest. Furthermore, the reference sign 22 refers to a landmark or marker in a star shape. The step a) relates to the time of planning and generation of a pre-image (in particular CT image). At the time of FIG. 2a, the bony structure 110 and the treatment body 100 have a relative position marked by $d_{1tb}$. This relative position is represented by the distance $d_{1tb}$ which represents the distance between the soft tissue (i.e. the treatment body part, e.g. the tumor) 100 and the bony structure (e.g. a bone) 100. Since the position of the soft tissue is set to coincide with the position of the treatment beam (which represents the position of the actual arrangement), the distance $d_{1tb}$ and $d_{1ab}$ are equal. The distance $d_{1ab}$ represents the original planned relative bone position. Furthermore, there is a relative position between the treatment body part 100 and the landmark or marker 22. This relative position is described as a distance $d_{1tm}$. At the time of planning, the position of the treatment beam 13' relative to the treatment body part 100 and/or relative to the bony structure is planned. The position of the planned treatment beam 13' represents the position of the planned arrangement in FIG. 2a. Furthermore, a relative position between the treatment body part 100 and a landmark or marker 22 visible or touchable at the surface of the body is noted $d_{1tm}$. The relative position between the bony structure and the marker or landmark 22 is noted $d_{1bm}$. Furthermore, the planned relative tissue position, the relative position between the treatment body part and the planned arrangement 13' is noted $d_{1tb}$.

FIG. 2b refers to a later point in time where the patient is in particular placed at a different couch as in case of FIG. 2a. The patient is in the so referred to as "pre-alignment position" (at the pre-alignment time). The pre-alignment position has been chosen under the assumption that the relative position $d_{2tm}$ between the treatment body part 100 and the landmarks or marker 22 and/or between the bony structure 110 and the marker or landmark 22 remains unchanged from the planning time to the pre-alignment time. However, as shown in FIG. 2b, the relative position $d_{2tm}$ between the treatment body part 100 and the landmark or marker 22 as well as the relative position $d_{2bm}$ between the bony structure 110 and the landmark or marker 22 has changed. This results in that the treatment body part is displaced with respect to the actual arrangement (represented by the actual treatment beam 13) by a pre-alignment distance $d_{2at}$, i.e. the relative position between the actual arrangement 13 and the treatment body part 100 does not correspond to the planned relative tissue position $d_{1at}$ described in FIG. 2a. Furthermore, the position $d_{2ab}$ of the bony structure 110 relative to the treatment beam 13 (which is referred to as bone CBCT position) does not correspond to the original planned relative bone position data. The planned relative position $d_{1at}=0$. Furthermore, the relative position between the treatment body part 100 and the bony structure 110 $d_{2tb}$ shown in FIG. 2b can be different from that shown in FIG. 2a. In particular, the actual arrangement 13 is set in accordance with the planning data under the assumption that the treatment body part 100 is set correctly and/or under the assumption that the relative position between the planned arrangement 13' and the landmark or marker 22 has to be identical with the relative position between the actual arrangement 13 and the marker or landmark 22 at the pre-alignment time. Thus, as a result of the pre-alignment, the actual arrangement 13 for instance can be set in a defined position with respect to at least one of the following: the treatment device 10, the landmark or marker 22, the couch 60, a reference system of the CBCT image and the one or more positions of the x-ray imaging geometry. The actual arrangement describes in particular a number of, in particular plurality of positions of the beam source 12 with respect to at least one of the following: the treatment device 10, the marker or landmark 22, the couch 60, a reference system of the CBCT image, and the one or more positions of the x-ray imaging geometry. This arrangement can be a multiplicity (manifold) of continuously or discretely adopted positions.

At the pre-alignment time shown in FIG. 2b, preferably a CBCT image is generated. Preferably, the relative position between the actual arrangement 13 and the CBCT image is known. The term "is known" means herein in particular that information representing the knowledge is stored in the data base and accessible by the data processing method. Preferably, the (segmental) pre-image generated at the planning time (FIG. 2a) is matched with the CBCT-image (of the pre-alignment time) in order to determine the relative position between the actual arrangement 13 and the treatment body part 100 and/or the bone CBCT position. Preferably, the matching is performed by registering the pre-image with respect to the CBCT-image. The matching (in particular registration) is preferably performed under the condition that the treatment body part at the planning time is matched with the treatment body part at the pre-alignment time and/or the bony structure at the planning time is matched with the bony structure of the pre-alignment time. The matching can be rigid or non-rigid. In particular the geometry (size and/or shape) of the treatment body part and/or body structure represented in the pre-image is matched (in particular registrated) with the geometry (size and/or shape) of the treatment part and/or bony structure described by the CBCT-image. Preferably, the matching (in particular registration) is performed such that the matching of the treatment body part and/or bony structure shown in the pre-image and the CBCT image is the only condition when matching (registering) the two images which is to be met or this condition is given higher weight than the matching of other parts of the anatomical structure. If the matching is based on either the treatment body part or the bony structure, positional shifts between the bony structure 110 and the treatment part 100 at the planning time (shown in FIG. 2a) and the bony structure 110 and the treatment body part 100 at the pre-alignment time can have no or only minor influence on the matching (in particular registration) process. As shown in FIGS. 2b and 2c, the relative position $d_{2tb}$ between the bony structure 110 and the treatment body part 100 differs from the relative position as shown in FIG. 2a at the alignment time but has no influence on the (correct) positioning of the treatment body part in step 2c). In particular, the updated planned relative bone position is determined based on the CBCT data so that the treatment body part is in the planned relative tissue position if the bony structure is in the updated planned relative bone position.

Preferably, based on the determined position $d_{2at}$ of the treatment body part 100 relative to the arrangement at the pre-alignment time and/or based on the determined position $d_{2ab}$ of the bony structure 110 relative to the arrangement 13 at the pre-alignment time (in step 2b) and based on the known position of the actual arrangement 13 in step 2b, the alignment control data are determined and output in order to control the position of the couch and/or the actual arrangement (relative to the treatment device 10). In particular, for this correction, only the position of the arrangement 13 is changed (if this is possible) with respect to the treatment device 10 since a movement of the couch 60 and thus of the patient 20 with respect to the treatment device 10 could have an influence on the relative position between the bony structure 110 and the treatment body part 100 (due to the influence of gravity). Of course, it is also within the gist of the present invention to control the position of the couch 60 and to thus change the position of the patient relative to the treatment device 10 based on the alignment control data. In particular the control is performed so that the position $d_{2ab}$ of the bony structure 110 relative to the arrangement 14 at the pre-alignment time.

FIG. 2c refers to the situation at the alignment time, i.e. the treatment body part has been aligned with the actual arrangement by means of the alignment control data. As shown in FIG. 2c, the alignment is correct, although the relative position $d_{2tb}$ between the treatment body part 100 and the bony structure 110 is different from the relative position $d_{1tb}$ shown in FIG. 2a. This is in particular due to the property of the CBCT image which shows both the bony structure and the soft tissue structure of which the treatment body part is a part. In particular, the matching is a rigid matching, i.e. without deformation of the images under the aforementioned conditions. The aforementioned registration is in particular performed by transforming the different sets of image data (e.g. the pre-image and the CBCT-image) into a common reference system.

After the treatment body part 100 and/or the bony structure 110 has been aligned in accordance FIG. 2c, preferably the treatment is started by issuing the treatment beam from the beam source 12 which adopts positions in accordance with the actual arrangement 13 so that the treatment beam adopts the positions of the actual arrangement 13. After some time (which may be at regular intervals or which may depend on the treatment plan or on the radiation dose or on other conditions) the position of the patient is monitored by means of generating x-ray images. FIG. 2d shows a schematic example for the situation at the monitoring time. The x-ray images represent a bony structure and in particular do not or (for matching purposes) not clearly enough represent the treatment body part. In particular, the relative position between the x-ray imaging geometries and the reference system of the CBCT image is known. Thus, by generating the DRRs from the CBCT image, the position $d_{4ab}$ of the bony structure 110 relative to the actual arrangement 13 (the so referred to as monitoring bone position) can be determined. Under the assumption that the relative position $d_{3tb}$ between the bony structure 110 and the treatment body part 100 at the monitoring time is the same as the relative position $d_{2tb}$ at the alignment time (step 2c), the position of the treatment body part 100 relative to the actual arrangement 13 can be determined. The relative position between the treatment body part 100 and the bony structure 110 is denoted as $d_{3tb}$. Thus, it is assumed that $d_{3tb}=d_{2tb}$. This assumption is generally more likely than assuming that $d_{2tb}=d_{1tb}$ since less time is elapsed between the situation shown in Figure c and the situation shown in Figure d and since the patient has not stood up or moved around between the alignment time and monitoring time but has only undergone small movements.

Based on the determined relative position $d_{4ab}$ between the bony structure 110 and the actual arrangement and based on the updated planned relative bone position or based on the position $d_{3ab}$ of the bony structure at the alignment time, the bone change (e.g. difference between $d_{4ab}$ and $d_{3ab}$) be determined Preferably based on the determined bone change, the x-ray based position control data are determined and outputted. The output control data cause in particular a change of position of the couch 60 and/or the actual arrangement 13 relative to the treatment body part. In particular, only the couch 60 is moved since it is to be assumed that the positional change is caused by a movement of the patient. Thus, a compensating movement of the couch 60 is likely to bring the anatomical structure which includes the bony structure 100 and the treatment body part 100 in the same relative position with respect to the gravity field as at the alignment time. This can increase the likelihood that the relative position between the bony structure 110 and the treatment body part 100 is the same as at the alignment time (after the correction has been performed in accordance with the x-ray based correction data). In summary, the x-ray based correction data (causing a movement of the couch and/or the actual arrangement) are likely to result in that $d_{4tb}$ is equal to $d_{3tb}$ and $d_{2tb}$, i.e. the relative positions are the same at the monitoring time and after the correction. In particular, the correction results in that the position $d_{5ab}$ of the bony structure (in step e)) corresponds to the position $d_{3ab}$ of the bony structure at the alignment time. Thus, the determined bone change is compensated. It is likely that the relative position $d_{5at}$ between the treatment body part 100 and the arrangement 13 is correct after the correction as shown in step 2e), i.e. after controlling the position of the bony structure to compensate the determined bone change.

FIG. 2f refers to a later point in time which is after the correction. In particular, between the time of correcting shown in FIG. 2e and the time of another monitoring (e.g. second or third monitoring etc.) there is a misalignment of the position $d_{5ab}$ of the bone structure 110 with respect to the actual arrangement 13. Again assuming that the relative position between the bony structure 110 and the treatment body part 100 (denoted as $d_{5tb}$) is the same as at the alignment time, i.e. $d_{5tb}=d_{2tb}$, then steps corresponding to the steps shown in FIGS. 2c, 2d, 2e, and 2f can be repeated. Thus, there is preferably a matching, in particular registration of the bony structure 110 of FIG. 2c with the bony structure 110 of FIG. 2f. This results in a determination of the position $d_{6ab}$ of the bony structure 110 with respect to the actual arrangement 13 and thus in a determination of the bone change, in particular of a difference between $d_{6ab}$ and $d_{3ab}$ or a difference between $d_{6ab}$ and $d_{5ab}$) This is done in a manner corresponding to step 2d. Based on the determined bone change, x-ray based correction data are output which result in a correction of the position of the bony structure 110 to be in line with the alignment bone position $d_{3ab}$ in a manner corresponding to step 2e). Then again a third monitoring corresponding to step 2f) can be performed.

According to an embodiment, the delivery of treatment radiation is interrupted after determining that a correction of the position is required and is continued after correcting the position.

Figure 3:
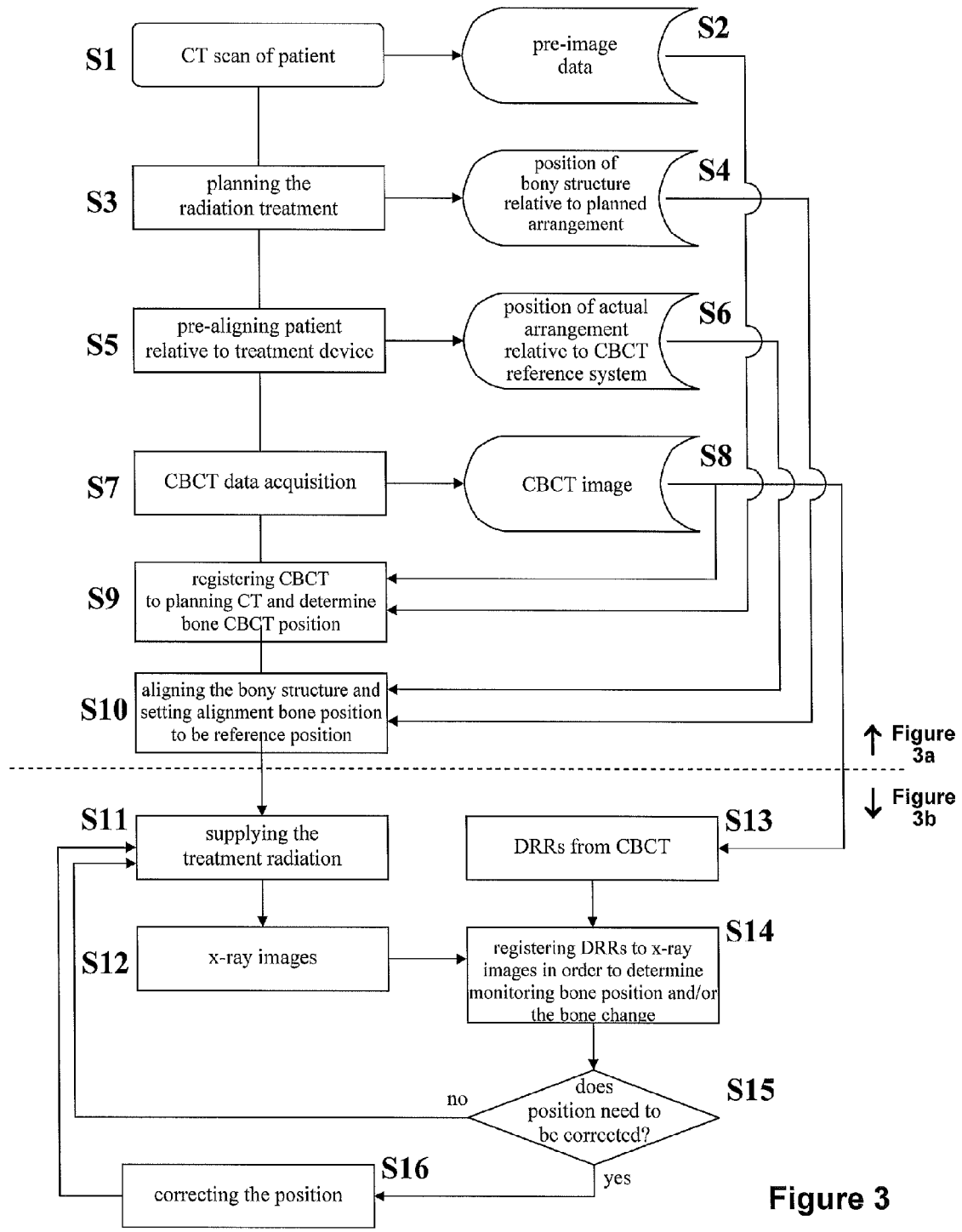

FIG. 3 shows a flow diagram explaining a sequence of steps in accordance with an embodiment of the invention. FIG. 3a relates to the steps until the alignment time and FIG. 3b relates to the steps after the alignment time and in particular to the steps during treatment of the treatment body part by means of the treatment radiation.

According to a step S1, a CT scan of a patient is performed which results in pre-image data which are stored in step S2. According to step S3 a radiation treatment planning is performed which results in an original planned relative bone position $d_{1ab}$ of the bony structure 100 relative to a planned arrangement 13' of beam positions. The original planned relative bone position $d_{1ab}$ (see FIG. 2a) is stored in step S4.

Usually after some hours or on another day, a patient is pre-aligned with respect to the treatment device 10 (e.g. placed on the couch 60 of the treatment system according to step S5). The actual arrangement 13 is set by an operator which results in that there is a known relative position of the actual arrangement 13 relative to treatment device 10 and thus relative to the CBCT reference system (within which the CBCT image is resting). This position of the actual arrangement 13 relative to the CBCT reference system is known to the data processing method and in particular available in a data storage by accessing the data storage (step S6). Then in step S7 the CBCT data are acquired in order to generate a three-dimensional CBCT image in step S8. In step S9 the three-dimensional CBCT image is registered to the three-dimensional CT image to determine the bone CBCT position $d_{2ab}$. In step S10 an alignment of the position of the bony structure is performed based on the registration S9 and based on the data of steps S4 and S6. The alignment results in a change from $d_{2ab}$ to $d_{3ab}$ (see FIGS. 2b to 2c).

FIG. 3b refers to the x-ray (and CBCT) based correction of the relative position between the actual arrangement and the anatomical structure. According to S11, the treatment is started and continued by delivering treatment radiation. After some time in step S12 x-ray images are generated (preferably stereoscopic x-ray images) for monitoring the position of the bony structure 110. In step S13 DRRs are generated from the three-dimensional CBCT image. In step S14 the DRRs are registered (FIG. 2d) to the x-ray images in order to determine a deviation of the monitoring bone position ($d_{4ab}$) from the alignment bone position $d_{3ab}$ (in particular under the assumption that the relative position between the treatment body part 100 and the bony structure 110 has not changed from the pre-alignment time to the monitoring time). The registration of the DRRs to the x-ray images allows to determine the position $d_{4ab}$ of the bony structure at the monitoring time relative to the actual arrangement. In particular the bone change is determined in step S14 by comparing the position of the bony structure 110 at the monitoring time and the position of the bony structure 110 at the alignment time, in particular by comparing the monitoring bone position $d_{4ab}$ with the alignment bone position (reference position) $d_{3ab}$.

In the step S15 it is checked whether a correction is required (for instance whether there is no bone change or the amount of bone change is above a predetermined threshold). If no correction is required, the delivery of the treatment radiation is continued. If a correction is required, then the correction is performed in step S16 (which results in the corrected position $d_{5ab}$ shown in FIG. 2e) and the delivery of radiation is continued after the correction by restarting the procedure at step S11. After some time of treatment, again x-ray images are generated according to step S12 which corresponds to the situation shown in FIG. 2f.

The invention claimed is:

1. Data processing method for use in the field of radiation therapy and for determining a relative position between a position of a bony structure and a reference position at a monitoring time after an alignment, the relative position being referred to as monitoring bone position, wherein an anatomical structure of an associated patient includes the bony structure and a treatment body part to be treated by at least one treatment beam of an associated treatment device, the reference position having a defined relative position with respect to an actual arrangement of at least one position of the at least one treatment beam; the data processing method being constituted to be performed by a computer and comprising:

providing cone beam computed tomography (CBCT) image data describing a three-dimensional CBCT image of the bony structure, the CBCT image representing the bony structure at a pre-alignment time before the alignment;

providing x-ray image data describing at least one two-dimensional x-ray image of the anatomical structure, the at least one two-dimensional x-ray image representing the bony structure and the x-ray image data being generated at the monitoring time;

providing imaging position data comprising at least one of CBCT position data and x-ray geometry data, CBCT position data describing the relative position between the CBCT image and the actual arrangement and x-ray geometry data describing a positional relationship between the actual arrangement and at least one imaging geometry, referred to as x-ray imaging geometry, given for generating the at least one x-ray image; and, determining the relative position between the bony structure and the reference position at the monitoring time on the basis of the CBCT image data, the x-ray image data and the imaging position data, wherein the determining the relative position between the position of the bony structure and the reference position comprises:

determining at least one two-dimensional digitally reconstructed radiograph from the three-dimensional CBCT image which matches the at least one x-ray image, the matching at least one two-dimensional digitally reconstructed radiograph resulting from a simulation of at least one imaging geometry given for generating the at least two-dimensional digitally reconstructed radiograph, the imaging geometry being referred to as matching imaging geometry, wherein the matching is performed based on the bony structure shown in both the at least one two-dimensional digitally reconstructed radiograph and the at least one x-ray image;

based on the matching, determining a relative position between the at least one matching imaging geometry and the at least one position described by the imaging position data, the relative position being referred to as matching position; and determining the monitoring bone position based on the imaging position data, the matching position and the position of the bony structure within the CBCT image described by the CBCT image data.

2. The method of claim 1, further comprising a step for determining a change of a relative position between the position of the bony structure and the reference position based on the determined relative position between the position of the bony structure and the reference position at the monitoring time and based on a relative position between the position of the bony structure and the reference position at a previous time before the monitoring time, the change being referred to as bone change, and the relative position at the previous time being referred to as previous relative position.

3. The method of claim 1,
wherein the reference position is a position referred to as bone CBCT position describing the relative position between the bony structure and the actual arrangement at the pre-alignment time, wherein the bone CBCT position is determined based on the CBCT data and the CBCT position data; or
wherein the reference position is the position of the actual arrangement; or
wherein the reference position is a position of the bony structure at a point in time referred to as previous monitoring time which is before the monitoring time and at which at least one two-dimensional x-ray image has been generated for determining the position of the bony structure at the previous monitoring time in the same manner as the monitoring bone position is determined in accordance with the method of claim 1; or
wherein target position data are provided which describe a target position which is a relative position between the position of the bony structure and the position of the actual arrangement, and wherein the reference position is the target position; or
wherein the method comprises the steps of:
determining a position referred to as bone CBCT position describing the relative position between the bony structure and the actual arrangement based on the CBCT data and the CBCT position data;
in case a of an alignment of the position of the anatomical structure after generation of the CBCT image, providing position alignment data describing the alignment of the position of the bony structure relative to the actual arrangement; and
in case of an alignment, determining a position referred to as alignment bone position which describes the relative position between the bony structure and the actual arrangement based on the bone CBCT position and the position alignment data, and
wherein, in case there was the alignment, the reference position is the alignment bone position.

4. The method of claim 1, further comprising a step for determining a change of a relative position between the position of the bony structure and the reference position based on the determined relative position between the position of the bony structure and the reference position at the monitoring time and based on a relative position between the position of the bony structure and the reference position at a previous time before the monitoring time, the change being referred to as bone change, and the relative position at the previous time being referred to as previous relative position
wherein the step of determining the bone change is at least one of the following:
a) a step of determining at least one of an amount and direction of the bone change, and
b) a step of determining whether there is the bone change; and
wherein the previous time is one of the following:
the pre-alignment time;
the alignment time; or
the previous monitoring time.

5. The method of claim 1, wherein the x-ray geometry data further describe information on a size of the presented bony structure in dependence on the position of the bony structure with respect to the imaging geometry.

6. The method of claim 1, wherein the reference position is a position referred to as bone CBCT position describing the relative position between the bony structure and the actual arrangement at the pre-alignment time, wherein the bone CBCT position is determined based on the CBCT data and the CBCT position data; or
wherein the reference position is the position of the actual arrangement; or
wherein the reference position is a position of the bony structure at a point in time referred to as previous monitoring time which is before the monitoring time and at which at least one two-dimensional x-ray image has been generated for determining the position of the bony structure at the previous monitoring time in the same manner as the monitoring bone position is determined in accordance with the method of claim 1; or
wherein target position data are provided which describe a target position which is a relative position between the position of the bony structure and the position of the actual arrangement, and wherein the reference position is the target position; or
wherein the method comprises the steps of:
determining a position referred to as bone CBCT position describing the relative position between the bony structure and the actual arrangement based on the CBCT data and the CBCT position data;
in case a of an alignment of the position of the anatomical structure after generation of the CBCT image, providing position alignment data describing the alignment of the position of the bony structure relative to the actual arrangement; and in case of an alignment, determining a position referred to as alignment bone position which describes the relative position between the bony structure and the actual arrangement based on the bone CBCT position and the position alignment data, and wherein, in case there was the alignment, the reference position is the alignment bone position, wherein the monitoring bone position is determined based on the bone CBCT position as well as based on the difference between the position of the x-ray imaging geometry and the position of the matching imaging geometry.

7. The method of claim 6, wherein the target position resulted from a planning for the radiation therapy of the treatment body part, the planning being based on a CT image generated before the patient was placed for treatment by the at least one treatment beam.

8. A method for controlling the radiotherapy system of claim 1, comprising the steps of issuing control signals from the computer to at least one of the couch and the treatment device for changing the relative position between the couch and the arrangement.

9. A non-transitory program storage medium on which a program is stored which, when running on a computer or when loaded onto a computer, causes the computer to perform data processing steps for use in the field of radiation therapy and for determining a relative position between the position of a bony structure and a reference position at a monitoring time after an alignment, the relative position being referred to as monitoring bone position, wherein an anatomical structure of an associated patient includes the bony structure and a treatment body part to be treated by at least one treatment beam of an associated treatment device, the reference position having a defined relative position with respect to an actual arrangement of at least one position of the at least one treatment beam; the data processing steps being constituted to be performed by a computer and comprising:

providing cone beam computed tomography (CBCT) image data describing a three-dimensional CBCT image of the bony structure, the CBCT image representing the bony structure at a pre-alignment time before the alignment;

providing x-ray image data describing at least one two-dimensional x-ray image of the anatomical structure, the at least one two-dimensional x-ray image representing the bony structure and the x-ray image data being generated at the monitoring time;

providing imaging position data comprising at least one of CBCT position data and x-ray geometry data, CBCT position data describing the relative position between the CBCT image and the actual arrangement and x-ray geometry data describing a positional relationship between the actual arrangement and at least one imaging geometry, referred to as x-ray imaging geometry, given for generating the at least one x-ray image; and, determining the relative position between the bony structure and the reference position at the monitoring time on the basis of the CBCT image data, the x-ray image data and the imaging position data, wherein the determining the relative position between the position of the bony structure and the reference position comprises:

determining at least one two-dimensional digitally reconstructed radiograph from the three-dimensional CBCT image which matches the at least one x-ray image, the matching at least one two-dimensional digitally reconstructed radiograph resulting from a simulation of at least one imaging geometry given for generating the at least two-dimensional digitally reconstructed radiograph, the imaging geometry being referred to as matching imaging geometry, wherein the matching is performed based on the bony structure shown in both the at least one two-dimensional digitally reconstructed radiograph and the at least one x-ray image;

based on the matching, determining a relative position between the at least one matching imaging geometry and the at least one position described by the imaging position data, the relative position being referred to as matching position; and determining the monitoring bone position based on the imaging position data, the matching position and the position of the bony structure within the CBCT image described by the CBCT image data.

10. A computer which comprises the non-transitory program storage medium of claim 9.

11. A radiotherapy system, comprising:

the computer of claim 10;

the treatment device for treating the treatment body part with the actual arrangement;

a couch for placing the patient, the treatment device constituted for treating the treatment body part, if the patient is placed on the couch for treatment;

a CBCT-device constituted for generating the three-dimensional CBCT image and for generating the at least one x-ray image, if the patient is placed on the couch for treatment and for outputting the three-dimensional CBCT image and the at least one x-ray image to the computer; or a CBCT-device constituted for generating the three-dimensional CBCT image and for outputting the three-dimensional CBCT image to the computer, and an x-ray device for generating the at least one x-ray image, if the patient is placed on the couch for treatment, and for outputting the at least one x-ray image to the computer.

12. The radiotherapy system of claim 11, wherein the system is constituted so that the position of the couch relative to the position of the arrangement is controllable by the computer.

* * * * *